US008710183B2

(12) United States Patent
Grangeasse et al.

(10) Patent No.: US 8,710,183 B2
(45) Date of Patent: Apr. 29, 2014

(54) INHIBITORS OF BACTERIAL TYROSINE KINASE AND USES THEREOF

(75) Inventors: Christophe Louis Antoine Grangeasse, Messimy (FR); Sylvie Marianne Nessler, Vaugrigneuse (FR); Solange Rose Theodora Morera, Bures sur Yvettes (FR); Philippe Roger Meyer, Paris (FR); Alain Jean Cozzone, Caluire (FR); Raphael Terreux, Lyons (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 648 days.

(21) Appl. No.: 12/990,090

(22) PCT Filed: May 4, 2009

(86) PCT No.: PCT/EP2009/055366
§ 371 (c)(1),
(2), (4) Date: Jan. 7, 2011

(87) PCT Pub. No.: WO2009/133209
PCT Pub. Date: Nov. 5, 2009

(65) Prior Publication Data
US 2011/0130541 A1    Jun. 2, 2011

Related U.S. Application Data

(60) Provisional application No. 61/049,941, filed on May 2, 2008.

(51) Int. Cl.
 A61K 38/00     (2006.01)
 C07K 5/00      (2006.01)
 C07K 7/00      (2006.01)
 C07K 16/00     (2006.01)
 C07K 17/00     (2006.01)
 A61K 38/04     (2006.01)
(52) U.S. Cl.
 USPC ........... 530/324; 530/300; 530/325; 530/326; 530/327; 530/328; 530/329; 530/330
(58) Field of Classification Search
 None
 See application file for complete search history.

(56) References Cited

PUBLICATIONS

Jadeau et al "Identification of the idiosyncratic bacterial protein tyrosine kinase (BY-kinase) family signature" Bioinformatics 24:2427-2430. Published online Sep. 3, 2008.*
C Grangeasse et al, "Tyrosine phosphorylation: an emerging regulatory device of bacterial physiology", Feb. 2007, pp. 86-94, vol. 32, No. 2, Elsevier, Haywards.
Olivares-Illana et al, "Structural Basis for the Regulation Mechanism of the Tyrosine Kinase CapB from *Staphylococcus aureus*", Jun. 2008, pp. 1321-1331, vol. 6, No. 6.
O'Riordan et al, "*Staphylococcus aureus* Capsular Polysaccharides", Jan. 2004, pp. 218-234, vol. 17, No. 1, Clinical Microbiology Reviews.
Niemeyer et al, "The Molecular Weight Distribution of Succinoglycan Produced by *Sinorhizobium meliloti* Is Influenced by Specific Tyrosine Phosphorylation and ATPase Activity of Cytoplasmic Domain of the ExoP Protein", Sep. 2001, pp. 5163-5170, vol. 183, No. 17, Journal of Bacteriology.
Naker et al, "Involvement of a Protein Tyrosine Kinase in Production of the Polymeric Biomulsifier Emulsan from the Oil-Degrading Strain Aninetobacter lwoffii RAG-1", Feb. 2003, pp. 1001-1009, vol. 185, No. 3, Journal of Bacteriology.
Obadia et al, "Influence of Tyrosine-Kinase Wzc Activity on Colanic Acid Production in *Escherichia coli* K12 Cells", 2007, pp. 42-53, vol. 367, J. Mol. Biol.
Saraste et al, "The P-loop—a common motif in ATP-and GTP-binding proteins", 1990, pp. 430-434 TIBS 15.
Cozzone, Alain J., "Protein Phosphorylation in Prokaryotes", 1988, pp. 97-125, vol. 42, Ann. Rev. Microbiol.
Cunnion et al, "Availability of Complement Bound to *Staphylococcus aureus* to Interact with Membrane Complement Receptors Influences Efficiency of Phagocytosis", Feb. 2003, pp. 656-662, vol. 71, No. 2, Infection and Immunity.
Cozzone et al, "Protein Phosphorylation on Tyrosine in Bacteria", 2004, pp. 171-181, vol. 181, Arch. Microbiol.
Deutscher et al, "How Phosphotransferase System-Related Protein Phosphorylation Regulates Carbohydrate Metabolism in Bacteria", Dec. 2006, pp. 939-1031, vol. 70, No. 4, Microbiology and Molecular Biology Reviews.
Deutscher et al, "Ser/Thr/Tyr Protein Phosphorylation in Bacteria—For Long Time Neglected Now Well Established", 2005, pp. 125-131, vol. 9, Journal of Molecular Microbiology and Biotechnology.
Grangeasse et al, "Autophosphorylation of the *Escherichia coli* Protein Kinase Wzc Regulates Tyrosine Phosphorylation of Ugd, a UDP-glucose Dehydrogenase", Oct. 10, 2003, pp. 39323-39329, vol. 278, No. 41, The Journal of Biological Chemistry.
Grangeasse et al, "Characterization of a bacterial gene encoding an autophosphorylating protein tyrosine kinase", 1997, pp. 259-265, Gene.
Fieulaine et al, "X-ray structure of a bifunctional protein kinase in complex with its protein substrate HPr", Oct. 15, 2002, pp. 13437-13441, vol. 99, No. 21, PNAS.
Shi et al, "The serine, threonine, and/or tyrosine-specific protein kinases and protein phosphatases of prokaryotic organisms: a family portrait", 1998, pp. 229-253, FEMS Microbiology Reviews 22.
Thakker et al, "*Staphylococcus aureus* Serotype 5 Capsular Polysaccharide Is Antiphagocytic and Enhances Bacterial Virulence in a Murine Bacteremia Model", Nov. 1998, pp. 5183-5189, vol. 66, No. 11, Infection and Immunity.
Whitfield, Chris, "Biosynthesis and Assembly of Capsular Polysaccharides in *Escherichia coli*", 2006, pp. 39-68, vol. 75, Annu. Rev. Biochem.
Petranovic et al, "*Bacillus subtilis* strain deficient for the protein-tyrosine kinase PtkA exhibits impaired DNA replication", 2007, pp. 1797-1805, vol. 63, No. 6, Molecular Microbiology.

(Continued)

*Primary Examiner* — Cecilia J Tsang
*Assistant Examiner* — Zachary J Miknis
(74) *Attorney, Agent, or Firm* — B. Aaron Schulman, Esq.; Stites & Harbison, PLLC.

(57) ABSTRACT

A compound comprising a peptide moiety comprising, consisting essentially of, or consisting of, the peptide sequence of a tyrosine cluster YC of the BY-kinase of a Gram positive or Gram negative bacteria, or a fragment or an analogue thereof, and an adenine peptide analogue PNA(A), whereas the peptide moiety and the PNA are linked together. The compound is useful as an inhibitor of bacterial tyrosine kinase.

34 Claims, No Drawings

(56) References Cited

PUBLICATIONS

Soulat et al, "UDP-Acetyl-Mannosamine Dehydrogenase Is an Endogenous Protein Substrate of *Staphylococcus aureus* Protein-Tyrosine Kinase Activity", 2007, pp. 45-54, vol. 13, J. Mol. Microbiol. Biotechnol.

Roberts, Ian S., "The Biochemistry and Genetics of Capsular Polysaccharide Production in Bacteria", 1996, pp. 285-315, Annu. Rev. Microbiol.

Reizer et al, "A novel protein kinase that controls carbon catabolite repression in bacteria", 1998, pp. 1157-1169, vol. 27, No. 6, Molecular Microbiology.

Mijakovic et al, "Bacterial single-stranded DNA-binding proteins are phosphorylated on tyrosine", 2006, pp. 1588-1596, vol. 34, No. 5, Nucleic Acids Research.

Macek et al, "Phosphoproteome Analysis of *E. coli* Reveals Evolutionary Conservation of Bacterial Ser/Thr/Tyr Phosphorylation", 2008, pp. 299-307, Molecular & Cellular Proteomics 7. 2.

Macek et al, "The Serine/Threonine/Tyrosine Phosphoproteome of the Model Bacterium *Bacillus subtilis*", 2007, pp. 697-707, Molecular & Cellular Proteomics 6.4.

Mijakovic et al, Pyrophosphate-producing protein dephosphorylation by HPr kinase/phosphorylase: A relic of early life?

Mijakovic et al, "Transmembrane modulator-dependent bacterial tyrosine kinase activates UDP-glucose dehydrogenases", 2003, pp. 4709-4718, vol. 22, No. 18, The EMBO Journal.

Morona, "Evaluation of Wzz/MPA1/MPA2 proteins based on the presence of coiled-coli regions", Jan. 2000, pp. 1-5, Microbiology 146.

Kannan et al, "Did Protein Kinase Regulatory Mechanisms Evolve Through Elaboration of a Simple Structural Component?", 2005, pp. 956-972, vol. 351, J. Mol. Biol.

Lander, "Initial sequencing and analysis of the human genome", Feb. 15, 2001, pp. 860-921, vol. 409, Nature.

Karakawa et al, "Capsular Antibodies Induce Type-Specific Phagocytosis of Capsulated *Staphylococcus aureus* by Human Polymorphonuclear Leukocytes", May 1988, pp. 1090-1095, vol. 56, No. 5, Infection and Immunity.

Klein et al, "Phosphorylation-mediated regulation of heat shock response in *Escherichia coli*", 2003, pp. 269-285, vol. 48, No. 1, Molecular Microbiology.

Hoch, James A., "Two-component and phosphorelay signal transduction", 2000, pp. 165-170, Current Opinion in Microbiology.

Iyer et al, "Evolutionary History and Higher Order Classification of AAA+ ATPases", 2004, pp. 11-31, vol. 146, Journal of Structural Biology.

* cited by examiner

SEQUENCE LISTING

```
<160> NUMBER OF SEQ ID NOS: 68

<210> SEQ ID NO 1
<211> LENGTH: 17
<212> TYPE: PRT
<213> ORGANISM: Streptococcus pneumoniae

<400> SEQUENCE: 1

Ser Val Asp Lys Tyr Gly Val Tyr Gly Phe Tyr Gly Asn Tyr Gly Lys
1               5                   10                  15

Lys

<210> SEQ ID NO 2
<211> LENGTH: 17
<212> TYPE: PRT
<213> ORGANISM: Staphylococcus aureus

<400> SEQUENCE: 2

Lys Thr Lys Val Asp Lys Ser Ser Ser Tyr Tyr His Tyr Tyr Gly Asp
1               5                   10                  15

Glu

<210> SEQ ID NO 3
<211> LENGTH: 16
<212> TYPE: PRT
<213> ORGANISM: Staphylococcus aureus

<400> SEQUENCE: 3

Lys Asp Lys Ser Ala Ser Tyr Tyr Ala Tyr Tyr Gly Thr Asp Glu Ser
1               5                   10                  15

<210> SEQ ID NO 4
<211> LENGTH: 21
<212> TYPE: PRT
<213> ORGANISM: Escherichia coli

<400> SEQUENCE: 4

Lys Ala Ser Ser Tyr Tyr Arg Tyr Gly His Asn His Tyr Gly Tyr Ser
1               5                   10                  15

Tyr Tyr Asp Lys Lys
            20
```

<210> SEQ ID NO 5
<211> LENGTH: 21
<212> TYPE: PRT
<213> ORGANISM: Escherichia coli

<400> SEQUENCE: 5

Arg Arg Ala Ser Ala Tyr Gln Asp Tyr Gly Tyr Tyr Glu Tyr Glu Tyr
1               5                   10                  15

Lys Ser Asp Ala Lys
            20

<210> SEQ ID NO 6
<211> LENGTH: 22
<212> TYPE: PRT
<213> ORGANISM: Escherichia coli

<400> SEQUENCE: 6

Lys Arg Ala Ser Thr Ala Tyr Ser Tyr Gly Tyr Asn Tyr Tyr Gly Tyr
1               5                   10                  15

Ser Tyr Ser Glu Lys Glu
            20

<210> SEQ ID NO 7
<211> LENGTH: 21
<212> TYPE: PRT
<213> ORGANISM: Escherichia coli

<400> SEQUENCE: 7

Arg Arg Ala Ser Ala Tyr Gln Asp Tyr Gly Tyr Tyr Glu Tyr Glu Tyr
1               5                   10                  15

Lys Ser Asp Ala Lys
            20

<210> SEQ ID NO 8
<211> LENGTH: 23
<212> TYPE: PRT
<213> ORGANISM: Erwinia amylovora

<400> SEQUENCE: 8

Lys Ser Ala Asn Asn Tyr Gly Tyr Gly Tyr Asp Tyr Tyr Asp Tyr Ser
1               5                   10                  15

Tyr Gln Gln Gly Glu Lys Ser
            20

<210> SEQ ID NO 9
<211> LENGTH: 22
<212> TYPE: PRT
<213> ORGANISM: Klebsiella pneumoniae

<400> SEQUENCE: 9

Lys Lys Ala Thr Asn Lys Tyr Gly Tyr Gly Tyr Asn Tyr Tyr Asp Tyr
1               5                   10                  15

Ser Tyr Ser Asp Lys Lys
            20

<210> SEQ ID NO 10
<211> LENGTH: 24
<212> TYPE: PRT
<213> ORGANISM: Acinetobacter johnsonii

<400> SEQUENCE: 10

Ser Ser Ala Gly Tyr Gly Tyr Gly Tyr Gly Tyr Asn Tyr Ala Tyr Ala
1               5                   10                  15

-continued

Tyr Lys Ala Asn Lys Glu Ser Asp
            20

<210> SEQ ID NO 11
<211> LENGTH: 35
<212> TYPE: PRT
<213> ORGANISM: Ralstonia solanacearum

<400> SEQUENCE: 11

Asp Pro Asn Thr Tyr Arg Tyr Gly Tyr Gly Ser Arg Tyr Gly Arg Tyr
1               5                   10                  15

Arg Tyr Val Gln Tyr Gly Tyr Thr Ser Asn Ser Lys Pro Pro Glu Ala
            20                  25                  30

Glu Ser Ala
        35

<210> SEQ ID NO 12
<211> LENGTH: 20
<212> TYPE: PRT
<213> ORGANISM: Shigella flexneri

<400> SEQUENCE: 12

Arg Ala Ser Ala Tyr Gln Asp Tyr Gly Tyr Tyr Glu Tyr Glu Tyr Lys
1               5                   10                  15

Ser Asp Ala Lys
            20

<210> SEQ ID NO 13
<211> LENGTH: 20
<212> TYPE: PRT
<213> ORGANISM: Salmonella typhi

<400> SEQUENCE: 13

Arg Ala Thr Gly Tyr Gln Asp Tyr Gly Tyr Tyr Glu Tyr Glu Tyr Gln
1               5                   10                  15

Ser Asp Ser Lys
            20

<210> SEQ ID NO 14
<211> LENGTH: 26
<212> TYPE: PRT
<213> ORGANISM: Vibrio cholerae

<400> SEQUENCE: 14

Lys Lys Ala Ser Arg Tyr Ser Gly Tyr Tyr His Tyr Gln Ala Tyr Tyr
1               5                   10                  15

Gly Glu Glu Thr Lys Ser Gly Ala Ala Lys
            20                  25

<210> SEQ ID NO 15
<211> LENGTH: 14
<212> TYPE: PRT
<213> ORGANISM: Artificial Sequence
<220> FEATURE:
<223> OTHER INFORMATION: YC

<400> SEQUENCE: 15

Asp Lys Tyr Gly Val Tyr Gly Phe Tyr Gly Asn Tyr Gly Lys
1               5                   10

<210> SEQ ID NO 16
<211> LENGTH: 9
<212> TYPE: PRT

```
<213> ORGANISM: Artificial Sequence
<220> FEATURE:
<223> OTHER INFORMATION: YC

<400> SEQUENCE: 16

Ser Ser Tyr Tyr His Tyr Tyr Gly Asp
1               5

<210> SEQ ID NO 17
<211> LENGTH: 9
<212> TYPE: PRT
<213> ORGANISM: Artificial Sequence
<220> FEATURE:
<223> OTHER INFORMATION: YC

<400> SEQUENCE: 17

Ala Ser Tyr Tyr Ala Tyr Tyr Gly Thr
1               5

<210> SEQ ID NO 18
<211> LENGTH: 8
<212> TYPE: PRT
<213> ORGANISM: Artificial Sequence
<220> FEATURE:
<223> OTHER INFORMATION: YC

<400> SEQUENCE: 18

Ser Ser Tyr Tyr Arg Tyr Gly His
1               5

<210> SEQ ID NO 19
<211> LENGTH: 10
<212> TYPE: PRT
<213> ORGANISM: Artificial Sequence
<220> FEATURE:
<223> OTHER INFORMATION: YC

<400> SEQUENCE: 19

Asn His Tyr Gly Tyr Ser Tyr Tyr Asp Lys
1               5                   10

<210> SEQ ID NO 20
<211> LENGTH: 15
<212> TYPE: PRT
<213> ORGANISM: Artificial Sequence
<220> FEATURE:
<223> OTHER INFORMATION: YC

<400> SEQUENCE: 20

Ser Ala Tyr Gln Asp Tyr Gly Tyr Tyr Glu Tyr Glu Tyr Lys Ser
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: YC

<400> SEQUENCE: 21

Thr Ala Tyr Ser Tyr Gly Tyr Asn Tyr Tyr Gly Tyr Ser Tyr Ser Glu
1               5                   10                  15

<210> SEQ ID NO 22
<211> LENGTH: 15
<212> TYPE: PRT
<213> ORGANISM: Artificial Sequence
<220> FEATURE:
```

<223> OTHER INFORMATION: YC

<400> SEQUENCE: 22

Ser Ala Tyr Gln Asp Tyr Gly Tyr Tyr Glu Tyr Glu Tyr Lys Ser
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: YC

<400> SEQUENCE: 23

Asn Asn Tyr Gly Tyr Gly Tyr Asp Tyr Asp Tyr Ser Tyr Gln Gln
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: YC

<400> SEQUENCE: 24

Asn Lys Tyr Gly Tyr Gly Tyr Asn Tyr Asp Tyr Ser Tyr Ser Asp
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: YC

<400> SEQUENCE: 25

Ala Gly Tyr Gly Tyr Gly Tyr Gly Tyr Asn Tyr Ala Tyr Ala Tyr Lys
1               5                   10                  15
Ala

<210> SEQ ID NO 26
<211> LENGTH: 9
<212> TYPE: PRT
<213> ORGANISM: Artificial Sequence
<220> FEATURE:
<223> OTHER INFORMATION: YC

<400> SEQUENCE: 26

Asn Thr Tyr Arg Tyr Gly Tyr Gly Ser
1               5

<210> SEQ ID NO 27
<211> LENGTH: 15
<212> TYPE: PRT
<213> ORGANISM: Artificial Sequence
<220> FEATURE:
<223> OTHER INFORMATION: YC

<400> SEQUENCE: 27

Ser Arg Tyr Gly Arg Tyr Arg Tyr Val Gln Tyr Gly Tyr Thr Ser
1               5                   10                  15

<210> SEQ ID NO 28
<211> LENGTH: 15
<212> TYPE: PRT
<213> ORGANISM: Artificial Sequence
<220> FEATURE:

```
<223> OTHER INFORMATION: YC

<400> SEQUENCE: 28

Ser Ala Tyr Gln Asp Tyr Gly Tyr Tyr Glu Tyr Glu Tyr Lys Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: YC

<400> SEQUENCE: 29

Thr Gly Tyr Gln Asp Tyr Gly Tyr Tyr Glu Tyr Glu Tyr Gln Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: YC

<400> SEQUENCE: 30

Ser Arg Tyr Ser Gly Tyr Tyr His Tyr Gln Ala Tyr Tyr Gly Glu
1               5                   10                  15

<210> SEQ ID NO 31
<211> LENGTH: 10
<212> TYPE: PRT
<213> ORGANISM: Artificial Sequence
<220> FEATURE:
<223> OTHER INFORMATION: YC fragment

<400> SEQUENCE: 31

Lys Tyr Gly Val Tyr Gly Phe Tyr Gly Asn
1               5                   10

<210> SEQ ID NO 32
<211> LENGTH: 5
<212> TYPE: PRT
<213> ORGANISM: Artificial Sequence
<220> FEATURE:
<223> OTHER INFORMATION: YC fragment

<400> SEQUENCE: 32

Ser Tyr Tyr His Tyr
1               5

<210> SEQ ID NO 33
<211> LENGTH: 6
<212> TYPE: PRT
<213> ORGANISM: Artificial Sequence
<220> FEATURE:
<223> OTHER INFORMATION: YC fragment

<400> SEQUENCE: 33

His Tyr Gly Tyr Ser Tyr
1               5

<210> SEQ ID NO 34
<211> LENGTH: 12
<212> TYPE: PRT
<213> ORGANISM: Artificial Sequence
<220> FEATURE:
<223> OTHER INFORMATION: YC fragment
```

```
<400> SEQUENCE: 34

Ala Tyr Ser Tyr Gly Tyr Asn Tyr Tyr Gly Tyr Ser
1               5                   10

<210> SEQ ID NO 35
<211> LENGTH: 12
<212> TYPE: PRT
<213> ORGANISM: Artificial Sequence
<220> FEATURE:
<223> OTHER INFORMATION: YC fragment

<400> SEQUENCE: 35

Asn Tyr Gly Tyr Gly Tyr Asp Tyr Tyr Asp Tyr Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: YC fragment

<400> SEQUENCE: 36

Lys Tyr Gly Tyr Gly Tyr Asn Tyr Tyr Asp Tyr Ser
1               5                   10

<210> SEQ ID NO 37
<211> LENGTH: 12
<212> TYPE: PRT
<213> ORGANISM: Artificial Sequence
<220> FEATURE:
<223> OTHER INFORMATION: YC fragment

<400> SEQUENCE: 37

Gly Tyr Gly Tyr Gly Tyr Gly Tyr Asn Tyr Ala Tyr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: YC fragment

<400> SEQUENCE: 38

Asp Tyr Gly Tyr Tyr Glu Tyr Glu
1               5

<210> SEQ ID NO 39
<211> LENGTH: 7
<212> TYPE: PRT
<213> ORGANISM: Artificial Sequence
<220> FEATURE:
<223> OTHER INFORMATION: peptide moiety

<400> SEQUENCE: 39

Ser Ala Ser Tyr Tyr Ala Tyr
1               5

<210> SEQ ID NO 40
<211> LENGTH: 7
<212> TYPE: PRT
<213> ORGANISM: Artificial Sequence
<220> FEATURE:
<223> OTHER INFORMATION: peptide moiety

<400> SEQUENCE: 40
```

```
Glu Ser Ser Tyr Gly Ala Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: peptide moiety

<400> SEQUENCE: 41

Lys His Ser Glu Tyr Gly Tyr
1               5

<210> SEQ ID NO 42
<211> LENGTH: 7
<212> TYPE: PRT
<213> ORGANISM: Artificial Sequence
<220> FEATURE:
<223> OTHER INFORMATION: peptide moiety

<400> SEQUENCE: 42

Tyr Asn Tyr Tyr Gly Tyr Ser
1               5

<210> SEQ ID NO 43
<211> LENGTH: 7
<212> TYPE: PRT
<213> ORGANISM: Artificial Sequence
<220> FEATURE:
<223> OTHER INFORMATION: peptide moiety

<400> SEQUENCE: 43

Lys His Ser Glu Gly Glu Tyr
1               5

<210> SEQ ID NO 44
<211> LENGTH: 7
<212> TYPE: PRT
<213> ORGANISM: Artificial Sequence
<220> FEATURE:
<223> OTHER INFORMATION: peptide moiety

<400> SEQUENCE: 44

Ser Ser Ser Tyr Tyr His Tyr
1               5

<210> SEQ ID NO 45
<211> LENGTH: 7
<212> TYPE: PRT
<213> ORGANISM: Artificial Sequence
<220> FEATURE:
<223> OTHER INFORMATION: peptide moiety

<400> SEQUENCE: 45

Val Tyr Gly Phe Tyr Gly Asn
1               5

<210> SEQ ID NO 46
<211> LENGTH: 12
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (12)..(12)
<223> OTHER INFORMATION: Xaa is PNA(A)
```

-continued

```
<400> SEQUENCE: 46

Lys Tyr Gly Val Tyr Gly Phe Tyr Gly Asn Lys Xaa
1               5                   10

<210> SEQ ID NO 47
<211> LENGTH: 7
<212> TYPE: PRT
<213> ORGANISM: Artificial Sequence
<220> FEATURE:
<223> OTHER INFORMATION: peptide moiety - PNA(A)
<220> FEATURE:
<221> NAME/KEY: MISC_FEATURE
<222> LOCATION: (7)..(7)
<223> OTHER INFORMATION: Xaa is PNA(A)

<400> SEQUENCE: 47

Ser Tyr Tyr His Tyr Lys Xaa
1               5

<210> SEQ ID NO 48
<211> LENGTH: 8
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (8)..(8)
<223> OTHER INFORMATION: Xaa is PNA(A)

<400> SEQUENCE: 48

His Tyr Gly Tyr Ser Tyr Lys Xaa
1               5

<210> SEQ ID NO 49
<211> LENGTH: 14
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (14)..(14)
<223> OTHER INFORMATION: Xaa is PNA(A)

<400> SEQUENCE: 49

Ala Tyr Ser Tyr Gly Tyr Asn Tyr Tyr Gly Tyr Ser Lys Xaa
1               5                   10

<210> SEQ ID NO 50
<211> LENGTH: 14
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (14)..(14)
<223> OTHER INFORMATION: Xaa is PNA(A)

<400> SEQUENCE: 50

Asn Tyr Gly Tyr Gly Tyr Asp Tyr Tyr Asp Tyr Ser Lys Xaa
1               5                   10

<210> SEQ ID NO 51
<211> LENGTH: 14
<212> TYPE: PRT
<213> ORGANISM: Artificial Sequence
<220> FEATURE:
<223> OTHER INFORMATION: peptide moiety-PNA(A)
```

```
<220> FEATURE:
<221> NAME/KEY: MISC_FEATURE
<222> LOCATION: (14)..(14)
<223> OTHER INFORMATION: Xaa is PNA(A)

<400> SEQUENCE: 51

Lys Tyr Gly Tyr Gly Tyr Asn Tyr Tyr Asp Tyr Ser Lys Xaa
1               5                   10

<210> SEQ ID NO 52
<211> LENGTH: 14
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (14)..(14)
<223> OTHER INFORMATION: Xaa is PNA(A)

<400> SEQUENCE: 52

Gly Tyr Gly Tyr Gly Tyr Gly Tyr Asn Tyr Ala Tyr Lys Xaa
1               5                   10

<210> SEQ ID NO 53
<211> LENGTH: 10
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (10)..(10)
<223> OTHER INFORMATION: Xaa is PNA(A)

<400> SEQUENCE: 53

Asp Tyr Gly Tyr Tyr Glu Tyr Glu Lys Xaa
1               5                   10

<210> SEQ ID NO 54
<211> LENGTH: 12
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (12)..(12)
<223> OTHER INFORMATION: Xaa is PNA(A)

<400> SEQUENCE: 54

Lys Tyr Gly Val Tyr Gly Phe Tyr Gly Asn Gly Xaa
1               5                   10

<210> SEQ ID NO 55
<211> LENGTH: 7
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (7)..(7)
<223> OTHER INFORMATION: Xaa is PNA(A)

<400> SEQUENCE: 55

Ser Tyr Tyr His Tyr Gly Xaa
1               5

<210> SEQ ID NO 56
```

```
<211> LENGTH: 8
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (8)..(8)
<223> OTHER INFORMATION: Xaa is PNA(A)

<400> SEQUENCE: 56

His Tyr Gly Tyr Ser Tyr Gly Xaa
1               5

<210> SEQ ID NO 57
<211> LENGTH: 14
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (14)..(14)
<223> OTHER INFORMATION: Xaa is PNA(A)

<400> SEQUENCE: 57

Ala Tyr Ser Tyr Gly Tyr Asn Tyr Tyr Gly Tyr Ser Gly Xaa
1               5                   10

<210> SEQ ID NO 58
<211> LENGTH: 14
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (14)..(14)
<223> OTHER INFORMATION: Xaa is PNA(A)

<400> SEQUENCE: 58

Asn Tyr Gly Tyr Gly Tyr Asp Tyr Tyr Asp Tyr Ser Gly Xaa
1               5                   10

<210> SEQ ID NO 59
<211> LENGTH: 14
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (14)..(14)
<223> OTHER INFORMATION: Xaa is PNA(A)

<400> SEQUENCE: 59

Lys Tyr Gly Tyr Gly Tyr Asn Tyr Tyr Asp Tyr Ser Gly Xaa
1               5                   10

<210> SEQ ID NO 60
<211> LENGTH: 14
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (14)..(14)
<223> OTHER INFORMATION: Xaa is PNA(A)

<400> SEQUENCE: 60
```

-continued

Gly Tyr Gly Tyr Gly Tyr Gly Tyr Asn Tyr Ala Tyr Gly Xaa
1               5                   10

<210> SEQ ID NO 61
<211> LENGTH: 10
<212> TYPE: PRT
<213> ORGANISM: Artificial Sequence
<220> FEATURE:
<223> OTHER INFORMATION: peptide moiety-PNA(A)
<220> FEATURE:
<221> NAME/KEY: MISC_FEATURE
<222> LOCATION: (10)..(10)
<223> OTHER INFORMATION: Xaa is PNA(A)

<400> SEQUENCE: 61

Asp Tyr Gly Tyr Tyr Glu Tyr Glu Gly Xaa
1               5                   10

<210> SEQ ID NO 62
<211> LENGTH: 12
<212> TYPE: PRT
<213> ORGANISM: Artificial Sequence
<220> FEATURE:
<223> OTHER INFORMATION: peptide moiety-PNA(A)-peptide moiety
<220> FEATURE:
<221> NAME/KEY: MISC_FEATURE
<222> LOCATION: (9)..(9)
<223> OTHER INFORMATION: Xaa is PNA(A)

<400> SEQUENCE: 62

Ser Ala Ser Tyr Tyr Ala Tyr Lys Xaa Gly Thr Asp
1               5                   10

<210> SEQ ID NO 63
<211> LENGTH: 12
<212> TYPE: PRT
<213> ORGANISM: Artificial Sequence
<220> FEATURE:
<223> OTHER INFORMATION: peptide moiety-PNA(A)-peptide moiety
<220> FEATURE:
<221> NAME/KEY: MISC_FEATURE
<222> LOCATION: (9)..(9)
<223> OTHER INFORMATION: Xaa is PNA(A)

<400> SEQUENCE: 63

Glu Ser Ser Tyr Gly Ala Tyr Lys Xaa Gly Thr Asp
1               5                   10

<210> SEQ ID NO 64
<211> LENGTH: 12
<212> TYPE: PRT
<213> ORGANISM: Artificial Sequence
<220> FEATURE:
<223> OTHER INFORMATION: peptide moiety-PNA(A)-peptide moiety
<220> FEATURE:
<221> NAME/KEY: MISC_FEATURE
<222> LOCATION: (9)..(9)
<223> OTHER INFORMATION: Xaa is PNA(A)

<400> SEQUENCE: 64

Lys His Ser Glu Tyr Gly Tyr Lys Xaa Gly Thr Lys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: peptide moiety-PNA(A)-peptide moiety
<220> FEATURE:
<221> NAME/KEY: MISC_FEATURE -continued

```
<222> LOCATION: (9)..(9)
<223> OTHER INFORMATION: Xaa is PNA(A)

<400> SEQUENCE: 65

Tyr Asn Tyr Tyr Gly Tyr Ser Lys Xaa Ser Glu Lys
1               5                   10

<210> SEQ ID NO 66
<211> LENGTH: 12
<212> TYPE: PRT
<213> ORGANISM: Artificial Sequence
<220> FEATURE:
<223> OTHER INFORMATION: peptide moiety-PNA(A)-peptide moiety
<220> FEATURE:
<221> NAME/KEY: MISC_FEATURE
<222> LOCATION: (9)..(9)
<223> OTHER INFORMATION: Xaa is PNA(A)

<400> SEQUENCE: 66

Lys His Ser Glu Gly Glu Tyr Lys Xaa Glu Thr Lys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: peptide moiety-PNA(A)-peptide moiety
<220> FEATURE:
<221> NAME/KEY: MISC_FEATURE
<222> LOCATION: (9)..(9)
<223> OTHER INFORMATION: Xaa is PNA(A)

<400> SEQUENCE: 67

Ser Ser Ser Tyr Tyr His Tyr Lys Xaa Gly Asp Glu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: peptide moiety-PNA(A)-peptide moiety
<220> FEATURE:
<221> NAME/KEY: MISC_FEATURE
<222> LOCATION: (9)..(9)
<223> OTHER INFORMATION: Xaa is PNA(A)

<400> SEQUENCE: 68

Val Tyr Gly Phe Tyr Gly Asn Lys Xaa Gly Lys Lys
1               5                   10
```

INHIBITORS OF BACTERIAL TYROSINE KINASE AND USES THEREOF

CROSS REFERENCE TO RELATED APPLICATIONS

This application claims benefit of U.S. Provisional Application No. 61/049,941, filed May 2, 2008 (which is hereby incorporated by reference).

FIELD OF THE INVENTION

The present invention relates to the field of bacterial tyrosine kinases and, in particular, to inhibitors thereof.

BACKGROUND OF THE INVENTION

Protein phosphorylation-dephosphorylation represents one of the most powerful and versatile mechanisms of molecular regulation in living organisms. For many years, however, protein phosphorylation-dephosphorylation was considered to be exclusive to eukaryotes. It was only after a long period of controversy that the existence of this modification was documented in bacteria (for a review, see [1]). Early studies essentially focused on the characterization of the "two-component system" [2] and "phosphotransferase PTS system" [3], the well-known hallmarks of bacterial signalling and regulation in which proteins are phosphorylated on histidines and aspartic acids. Then, thanks in large part to genomics the widespread presence of genes encoding eukaryotic-like serine/threonine kinases [4] and phosphatases has also turned out to be indisputable in bacteria [5]. In addition, high accuracy mass spectrometry experiments have recently allowed the characterization of more than one hundred of serine and threonine phosphorylation sites in two model bacteria [6,7].

Besides, some bacterial members of the large family of P-loop containing proteins [8,9] characterized by the Walker A nucleotide binding motif [10] were found to carry a protein kinase activity [11]. The first structurally [12] and functionally [13] characterized member of this new family of P-loop containing protein kinases was a serine kinase, the bifunctional HPr kinase/phosphorylase involved in a signalling pathway regulating the use of carbon sources by bacteria [14].

Progress on tyrosine phosphorylation in bacteria was slower and it was only in 1997 that the first gene encoding a bacterial tyrosine kinase was characterized [15]. This enzyme is structurally and functionally unrelated to its eukaryotic counterparts. Like the HPr kinase/phosphorylase, it belongs to the family of P-loop containing protein kinases. This particular type of tyrosine kinases has been identified in numerous bacteria [16] thus defining a bacterial idiosyncratic family of BY-kinases (for Bacterial tYrosine kinases) [17].

In proteobacteria and actinobacteria, BY-kinases are encoded as a single polypeptide whereas in firmicutes they are found in the form of two interacting proteins. The periplasmic N-terminal and the cytoplasmic C-terminal domains of BY-kinases from proteobacteria and actinobacteria are homologous to the membrane adaptator and the cytoplasmic BY-kinase from firmicutes, respectively. All BY-kinases that have been examined undergo autophosphorylation on a C-terminal tyrosine cluster, but also phosphorylate other proteins. Among the first identified endogenous protein substrates of BY-kinases were proteins involved in polysaccharide production [18-20] but also RNA polymerase sigma factors [21] and single-stranded DNA binding proteins [22]. Therefore, BY-kinases are implicated in many other important physiological processes including stress response, DNA metabolism, antibiotic resistance, control of the bacterial cell cycle, and pathogenicity [17,23].

The mechanism by which BY-kinases control extracellular polysaccharide biosynthesis is the best documented. Since 2000, an increasing number of publications have analyzed this process and tyrosine phosphorylation has turned out to be a key feature of capsule formation [24]. BY-kinases have been characterized as polysaccharide co-polymerases (PCP) belonging to multiprotein transmembrane machineries involved in synthesis and/or export of a large number of extracellular polysaccharides [25]. However, the accurate function of their phosphorylation remains unclear even if it has been shown to influence both the length and the amount of the produced polymer [26.-28], thus modifying the physico-chemical properties of the capsule [29]. Capsule play critical roles in the virulence of pathogenic bacteria. For instance, in bacterial human pathogens such as *Staphylococcus aureus*, capsule promotes virulence in animal models of infection [30,31]. The *S. aureus* capsule has been shown to be involved in protection against phagocytosis [32] and in modulation of the host immune response [33]. Therefore, bacterial tyrosine kinases can thus be considered as potential therapeutic targets.

SUMMARY OF THE INVENTION

An object of the present invention is to provide inhibitors of BY-kinases and uses thereof.

In accordance with one aspect of the present invention, there is provided a compound comprising a peptide moiety comprising, consisting essentially of, or consisting of, the peptide sequence of a tyrosine cluster of the BY-kinase of a bacteria, or a fragment or an analogue or derivative thereof, and an adenine peptide analogue PNA(A), whereas the peptide moiety and the PNA are linked together. The tyrosine cluster is a peptide ranging from 5 to 35 amino-acids (aa) long, more generally 5 to 20 aa, naturally found at the C-terminal end of bacterial tyrosine kinases, and that contains at least two tyrosine residues and up to 7. Examples are given thereafter.

According to a feature, the link between both species is a peptide bond. The compound may have a number of amino acid residues between 4 and 21, preferably between 5 and 15. This compound may act as a BY-kinase inhibitor.

According to a feature, the PNA(A) is linked at the C-terminal end of the peptide moiety.

According to another feature, the PNA(A) is linked to the peptide moiety through a K or G amino acid residue. This amino acid residue may be endogenous or not, and in the latter case, it is an added or inserted amino acid residue. The K or G may be a substituant of a Y residue of the peptide moiety.

According to another feature, the PNA(A) is linked at the C-terminal end of the peptide moiety through a K or G amino acid residue. This amino acid residue may be endogenous or not, and in the latter case, it is an added or inserted amino acid residue.

According to another feature, the compound has a number of amino acid residues between 4 and 21, preferably between 5 and 15.

In accordance with another aspect of the present invention, there is provided a pharmaceutical composition or drug comprising a compound as defined herein and a pharmaceutically acceptable diluent, carrier or excipient. This compound may act as a BY-kinase inhibitor.

According to a feature, the pharmaceutical composition or drug (medicament) of the invention comprises at least two such compounds each having a peptide moiety comprising, consisting essentially of, or consisting of, the peptide sequence of a naturally-occurring tyrosine cluster of the BY-kinase, or a fragment or an analogue thereof, of at least two different bacteriae.

In accordance with another aspect of the present invention, there is provided an inhibitor compound or pharmaceutical composition or drug of the invention for use in the treatment of a bacterial infection or in the prevention of a bacterial infection.

According to a feature, the pharmaceutical composition or drug of the invention comprises at least two such inhibitory compounds comprising, consisting essentially of, or consisting of, the peptide sequence of a naturally-occurring tyrosine cluster of the BY-kinase, or a fragment or an analogue thereof, of at least two different bacteriae, and the composition is used to treat or prevent a bacterial infection involving these several bacteriae.

In accordance with another aspect of the present invention, there is provided a use of such an inhibitor compound of the invention for the manufacture of a drug for use in the treatment of a bacterial infection or in the prevention of a bacterial infection.

According to a feature, the pharmaceutical composition or drug of the invention comprises at least two such inhibitory compounds having a peptide moiety comprising, consisting essentially of, or consisting of, the peptide sequence of a naturally-occurring tyrosine cluster of the BY-kinase, or a fragment or an analogue thereof, of at least two different bacteriae, and the composition is used to treat or prevent a bacterial infection involving these several bacteriae.

In accordance with another aspect of the present invention, there is provided a method of treating a subject against bacterial infection comprising administering to said subject an effective amount of a compound, pharmaceutical composition or drug of the invention.

In accordance with another aspect of the present invention, there is provided a method of preventing bacterial infection by a subject comprising administering to said subject an effective amount of a compound, pharmaceutical composition or drug of the invention.

According to a feature, the pharmaceutical composition or drug of the invention comprises at least two such inhibitory compounds having a peptide moiety comprising, consisting essentially of, or consisting of, the peptide sequence of a naturally-occurring tyrosine cluster of the BY-kinase, or a fragment or an analogue thereof, of at least two different bacteriae, and the method is used to prevent infection or treat infection by these several bacteriae.

DETAILED DESCRIPTION

Extracellular polysaccharides are considered as important virulence factors in pathogenic bacteria. The biosynthesis of polysaccharidic capsules involves most often enzymes termed polysaccharide co-polymerase (PCP). These PCPs also harbor a tyrosine autokinase activity and they are consequently also termed BY-kinases (for bacterial tyrosine kinases). It has been clearly established that the production of the polysaccharidic polymers was controlled by the tyrosine kinase activity of PCPs. Therefore, it could be envisaged that blocking the tyrosine kinase activity of PCPs will affect the ability of certain bacteria to produce extracellular polysaccharides and therefore their ability to infect an host and/or induce diseases.

An object of the invention is thus to provide for inhibitor compounds able to interfere with the tryrosine kinase activity and with the capsule formation.

Here, we mention a number of pathogenic bacteria, which encode a PCP that has been shown to influence somehow the production of their polysaccharide capsule. We indicate the amino acid sequence of their C-terminal end (i.e. the tyrosine cluster (YC) motif) that could be used to design a peptide-PNA inhibitor.

Gram-positive and gram-negative bacteria are contemplated herein.

Examples of bacteria and their tryrosine cluster sequence are given below for illustration but the recitation should not be considered in a limitative way.

*Streptococcus pneumoniae:*
  The leading cause of bacterial pneumoniae.
  Colonizes the upper respiratory tracts.
  Also cause otitis media, sinusitis, bacteremia and meningitis.
  Polysaccharidic capsule essential for invasive disease.
PCP/BY-kinase: CpsfD C-term end YC:    SVDKYGVYGFYGNYGKK    (SEQ ID NO: 1)

*Staphylococcus aureus:*
  Infection occurs most frequently when skin or mucosal barriers are breached and in hosts with compromised immune systems.
  Responsible for a diverse spectrum of disease.
  Invasive potential to induce osteomyelitis and endocarditis.
  Major role in nosocomial infection.
  Recent emergence of antibiotic-resistant strains (vancomycin, methicillin).
PCP/BY-kinase: CapB1 serotype 5

C-term end YC:    KTKVDKSSSYYHYYGDE    (SEQ ID NO: 2)

PCP/BY-kinase: CapB2 serotype 5

C-term end YC:    KDKSASYYAYYGTDES    (SEQ ID NO: 3)

*Escherichia coli:*
  Different serotypes: enterohemorrhagic (EHEC), enteropathogenic (EPEC), enterotoxigenic (ETEC), etc. . . .
  Responsible for severe illnesses such as haemorrhagic colitis, haemolytic uremic syndrome, infection of urinary tracts, diarrhea.
PCP/BY-kinase: Wzc of *E. coli* K30

```
                                        (SEQ ID NO: 4)
    C-term end YC:      KASSYYRYGHNHYGYSYYDKK
```

PCP/BY-kinase: Wzc of *E. coli* K12

```
                                        (SEQ ID NO: 5)
    C-term end YC:      RRASAYQDYGYYEYEYKSDAK
```

PCP/BY-kinase: Etk of *E. coli* K12

```
                                        (SEQ ID NO: 6)
    C-term end YC:      KRASTAYSYGYNYYGYSYSEKE
```

PCP/BY-kinase: Etk of *E. coli* O157:H7

```
                                            (SEQ ID NO: 7)
    C-term end YC:       RRASAYQDYGYYEYEYKSDAK
```

*Erwinia* species (*amylovora, carotovora, stewartii, chrysanthemi* . . . ):
  Cause soft rot diseases on many plant species.
  stewart's wilt on sweet corn, fire blight of maloideae (apple, pear and some ornamental trees etc. . . . ).
PCP/BY-kinase: AmsA of *E. amylovora*

```
                                            (SEQ ID NO: 8)
    C-term end YC:       KSANNYGYGYDYYDYSYQQGEKS
```

*Klebsiella pneumoniae:*
  Role in nosocomial infection.
  Pneumoniae or urinary tract infections.
  Also causes severe symptoms (liver abscess . . . ).
PCP/BY-kinase: Orf6

```
                                            (SEQ ID NO: 9)
    C-term end YC:       KKATNKYGYGYNYYDYSYSDKK
```

*Acinetobacter* species (*calcoaceticus, baumannii, johnsonii* . . . ):
  Very important nosocomial pathogens.
  Contribute to morbidity and mortality of patients particularly hospitalized in intensive care units.
  Recent emergence of antibiotic resistance strains (carbapenem).
PCP/BY-kinase: Ptk of *A. johnsonii*

```
                                            (SEQ ID NO: 10)
    C-term end YC:       SSAGYGYGYGY-NYAYAYKANKESD
```

*Pseudomonas* (*Rastonia*) *solanacearum:*
  Exopolysaccharide EPS I described as the primary virulence factor.
  Causes a lethal wilting disease of many types of plants.
  Infect via natural openings or wound in roots.
PCP/BY-kinase: EPSB

```
                                            (SEQ ID NO: 11)
    C-term end YC:
    DPNTYRYGYGSRYGRYRYVQYGYTSNSKPPEAESA
```

*Shigella* species (*flexneri, boydii, sonnei, dysenteriae*):
  Cause most communicable of bacterial dysenteries (shigellosis)
  Invade the colonic and rectal epithelium and induce severe inflammation and epithelial destruction.
  Patients may develop secondary complications (septicaemia, pneumoniae, haemolytic uremic syndrome).
  165 million cases each year (1.1 million deaths)
PCP/BY-kinase: SF2571 of *S. flexneri*

```
                                            (SEQ ID NO: 12)
    C-term end YC:       RASAYQDYGYYEYEYKSDAK
```

*Salmonella typhi:*
  Food born pathogen.
  Important humans and animal pathogens.
  Salmonellose.
  Infections result in enterocolitis with diarrhea and abdominal pain.
  Integrated resistance genes making a great risk to public health.
PCP/BY-kinase: ST2329 of CT18 strain

```
                                            (SEQ ID NO: 13)
    C-term end YC:       RATGYQDYGYYEYEYQSDSK
```

*Vibrio cholerae*
  Human pathogen.
  Capsule is critical for virulence in extraintestinal infections.
  Cause cholera.
  New emerged epidemic strains.
PCP/BY-kinase: VC0937

```
                                            (SEQ ID NO: 14)
    C-term end YC:       KKASRYSGYYHYQAYYGEETKSGAAK
```

In accordance with one aspect of the present invention, there is provided a compound comprising a peptide moiety comprising, consisting essentially of, or consisting of, the peptide sequence of a tyrosine cluster YC of the BY-kinase of a bacteria, or a fragment or an analogue or derivative thereof, and an adenine peptide analogue PNA(A), whereas the peptide moiety and the PNA are linked together. This compound may act as a BY-kinase inhibitor.

According to a feature, the link between both species is a peptide bond.

According to a feature, the YC is selected from one of SEQ ID NO: 1 to 14.

YC is a peptide ranging from 5 to 35, more generally 5 to 20 amino-acids long, naturally found at the C-terminal end of bacterial tyrosine kinases, and that contains at least two tyrosine residues and up to 7. The peptide moiety may have a number of amino acid residues of between 4 and 21, preferably between 5 and 15, more preferably between 7 and 11. The peptide moiety may have the sequence of a natural YC. As an alternative, it may contain a peptide fragment of a natural YC. It may also be a derivative, say it is an YC or has a peptide fragment of an YC, and the YC part has been modified to increase the affinity for the BY-kinase.

According to another feature, the YC is selected from the group consisting of:

| | |
|---|---|
| DKYGVYGFYGNYGK | (SEQ ID NO: 15) |
| SSYYHYYGD | (SEQ ID NO: 16) |
| ASYYAYYGT | (SEQ ID NO: 17) |
| SSYYRYGH | (SEQ ID NO: 18) |
| NHYGYSYYDK | (SEQ ID NO: 19) |
| SAYQDYGYYEYEYKS | (SEQ ID NO: 20) |
| TAYSYGYNYYGYSYSE | (SEQ ID NO: 21) |
| SAYQDYGYYEYEYKS | (SEQ ID NO: 22) |
| NNYGYGYDYYDYSYQQ | (SEQ ID NO: 23) |
| NKYGYGYNYYDYSYSD | (SEQ ID NO: 24) |
| AGYGYGYGYNYAYAYKA | (SEQ ID NO: 25) |
| NTYRYGYGS | (SEQ ID NO: 26) |
| SRYGRYRYVQYGYTS | (SEQ ID NO: 27) |

-continued

```
SAYQDYGYYEYEYKS        (SEQ ID NO: 28)

TGYQDYGYYEYEYQS        (SEQ ID NO: 29)

SRYSGYYHYQAYYGE        (SEQ ID NO: 30)
``` or a fragment thereof.

According to another feature, the peptide moiety is selected from the group consisting of the SEQ ID NO: 15 to 30.

According to another feature, the YC fragment is selected from the group consisting of:

```
KYGVYGFYGN             (SEQ ID NO: 31)

SYYHY                  (SEQ ID NO: 32)

HYGYSY                 (SEQ ID NO: 33)

AYSYGYNYYGYS           (SEQ ID NO: 34)

NYGYGYDYYDYS           (SEQ ID NO: 35)

KYGYGYNYYDYS           (SEQ ID NO: 36)

GYGYGYGYNYAY           (SEQ ID NO: 37)

DYGYYEYE               (SEQ ID NO: 38)
``` or a fragment thereof.

According to another feature, the peptide moiety is selected from the group consisting of the SEQ ID NO: 31 to 38.

In an embodiment concerning *S. aureus*, the peptide moiety comprises one of the following sequences:

```
SASYYAY                (SEQ ID NO: 39)

ESSYGAY                (SEQ ID NO: 40)

KHSEYGY                (SEQ ID NO: 41)

YNYYGYS                (SEQ ID NO: 42)

KHSEGEY                (SEQ ID NO: 43)

SSSYYHY                (SEQ ID NO: 44)

VYGFYGN                (SEQ ID NO: 45)
```

According to a feature, the PNA(A) is linked at the C-terminal end of the peptide moiety.

According to another feature, the PNA(A) is linked to the peptide moiety through a K or G amino acid residue. This amino acid residue may be endogenous or not, and in the latter case, it is an added or inserted amino acid residue.

According to another feature, the PNA(A) is linked at the C-terminal end of the peptide moiety through a K or G amino acid residue. The K or G amino acid residue may be endogenous or not, and in the latter case, it is an added or inserted amino acid residue. The K or G may be a substituant of a Y residue of the peptide moiety.

According to another feature, the compound has a number of amino acid residues between 4 and 21, preferably between 5 and 15.

In an embodiment concerning *S. aureus*, the compound is selected from the group of compounds BYK001, BYK002, BYK003, BYK004, BYK005, BYK006 and BYK007.

According to a preferred aspect, the invention relates to a compound, which may act as a BY-kinase inhibitor, which comprises a peptide moiety and one adenine peptide analogue PNA(A), wherein the combination of peptide moiety and PNA(A) has the general formula (I)

$$[U_a X_b Y_c Z_d]_e$$

wherein:
a is 0 or 1 and U represents an amino acid residue which can be every natural or artificial amino acid, D or L, in particular selected from A, C, D, E, F, G, H, I, K, L, M, N, P, Q, R, S, T, V, W and Y;
b is 0 or 1 and X represents an amino acid residue which can be every natural or artificial amino acid, D or L, in particular selected from A, C, D, E, F, G, H, I, K, L, M, N, P, Q, R, S, T, V, W and Y; preferably, X represents an amino acid residue selected from A, N, D, E, S and Y, in particular from D, E, S and Y;
a and b together can not be equal to 0
e is an integer selected from 2, 3, 4, 5, 6 and 7, preferably 3, 4 or 5; typically, the $[U_a X_b Y_c Z_d]$ units are different one from the other in the same peptide moiety;
Y is the amino acid Y, and c is 0 or 1
Z represents a moiety $J_f(PNA(A))$, wherein f is 0 or 1, preferably 1, and J represents the amino acid residue K or G;
d is 0 or 1, and c≠d;
PNA(A) is an adenine peptide analogue of general formula (II):

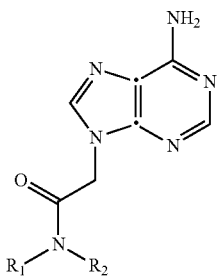

(XLI)

wherein:
$R_1$ and $R_2$ are independently an alkyl substituted with a carboxyl, carbonyl, alcohol or primary amino (i.e. —COOH, —C(O)R, where R is alkyl or H, —OH or —NH$_2$);
wherein PNA(A) is linked to the peptide moiety by formation of a peptide bond with a N-terminal NH$_2$ group or a C-terminal COOH group of K when J is K or with an amine group in the side chain of G when J is G;
wherein when J represents G, G is at a terminal position of the peptide moiety.

There is only one PNA(A) in the compound and therefore there is only one unit $[U_a X_b Y_c Z_d]$ where d=1. c=1 in the other units.

In an embodiment, the combination of peptide moiety and PNA(A) comprises the following moiety (II)

$$[UXY]_f[U_a X_b Z]$$

U, X, Y, Z, a and b being as above, and f is 1 or 2.

For example, BYK001 has this moiety with a=b=0 and U is Y, X is A and Z is K(PNA(A)).

The compound may contain other amino acids upstream and/or downstream formula (I) or (II) to get the 4-21 amino acid compound. The addition and selection of amino acids allows one to improve interaction affinity.

According to a feature, the compound comprises a peptide moiety which answers to the definition of the peptide moiety in formula (I) and is present in a tyrosine cluster of a bacteria.

According to an embodiment, the compound comprises a peptide moiety which answers to the definition of the peptide moiety in formula (I) and is present in a peptide formula selected from the group consisting of:

| | |
|---|---|
| SVDKYGVYGFYGNYGKK | (SEQ ID NO: 1) |
| KTKVDKSSSYYHYYGDE | (SEQ ID NO: 2) |
| KDKSASYYAYYGTDES | (SEQ ID NO: 3) |
| KASSYYRYGHNHYGYSYYDKK | (SEQ ID NO: 4) |
| RRASAYQDYGYYEYEYKSDAK | (SEQ ID NO: 5) |
| KRASTAYSYGYNYYGYSYSEKE | (SEQ ID NO: 6) |
| RRASAYQDYGYYEYEYKSDAK | (SEQ ID NO: 7) |
| KSANNYGYGYDYYDYSYQQGEKS | (SEQ ID NO: 8) |
| KKATNKYGYGYNYYDYSYSDKK | (SEQ ID NO: 9) |
| SSAGYGYGYGY-NYAYAYKANKESD | (SEQ ID NO: 10) |
| DPNTYRYGYGSRYGRYRYVQYGYTSNSKPPEAESA | (SEQ ID NO: 11) |
| RASAYQDYGYYEYEYKSDAK | (SEQ ID NO: 12) |
| RATGYQDYGYYEYEYQSDSK | (SEQ ID NO: 13) |
| KKASRYSGYYHYQAYYGEETKSGAAK. | (SEQ ID NO: 14) |

According to a preferred embodiment, the compound comprises a peptide moiety comprising one of the members or selected from the members of the group consisting of:

| | |
|---|---|
| DKYGVYGFYGNYGK | (SEQ ID NO: 15) |
| SSYYHYYGD | (SEQ ID NO: 16) |
| ASYYAYYGT | (SEQ ID NO: 17) |
| SSYYRYGH | (SEQ ID NO: 18) |
| NHYGYSYYDK | (SEQ ID NO: 19) |
| SAYQDYGYYEYEYKS | (SEQ ID NO: 20) |
| TAYSYGYNYYGYSYSE | (SEQ ID NO: 21) |
| SAYQDYGYYEYEYKS | (SEQ ID NO: 22) |
| NNYGYGYDYYDYSYQQ | (SEQ ID NO: 23) |
| NKYGYGYNYYDYSYSD | (SEQ ID NO: 24) |
| AGYGYGYGYNYAYAYKA | (SEQ ID NO: 25) |
| NTYRYGYGS | (SEQ ID NO: 26) |
| SRYGRYRYVQYGYTS | (SEQ ID NO: 27) |
| SAYQDYGYYEYEYKS | (SEQ ID NO: 28) |
| TGYQDYGYYEYEYQS | (SEQ ID NO: 29) |
| SRYSGYYHYQAYYGE | (SEQ ID NO: 30) | or a fragment or analogue thereof which answers to the definition in formula (I).

According to a more preferred embodiment, the compound comprises a peptide moiety comprising one of the members of the group consisting of:

| | |
|---|---|
| KYGVYGFYGN | (SEQ ID NO: 31) |
| SYYHY | (SEQ ID NO: 32) |
| HYGYSY | (SEQ ID NO: 33) |
| AYSYGYNYYGYS | (SEQ ID NO: 34) |
| NYGYGYDYYDYS | (SEQ ID NO: 35) |
| KYGYGYNYYDYS | (SEQ ID NO: 36) |
| GYGYGYGYNYAY | (SEQ ID NO: 37) |
| DYGYYEYE | (SEQ ID NO: 38) | or a fragment or analogue thereof which answers to the definition in formula (I).

According to another feature, J is the amino acid residue K and the PNA(A) is linked to the nitrogen atom of the lateral chain of this amino acid.

According to another feature, the amino acid residue K is at a terminal end of the peptide moiety.

According to another feature, the amino acid K is within the peptide moiety, it may be an endogenous amino acid or an added amino acid.

A preferred embodiment is a compound having a formula selected from:

| | |
|---|---|
| KYGVYGFYGNK(PNA(A)) | (SEQ ID NO: 46) |
| SYYHYK(PNA(A)) | (SEQ ID NO: 47) |
| HYGYSYK(PNA(A)) | (SEQ ID NO: 48) |
| AYSYGYNYYGYSK(PNA(A)) | (SEQ ID NO: 49) |
| NYGYGYDYYDYSK(PNA(A)) | (SEQ ID NO: 50) |
| KYGYGYNYYDYSK(PNA(A)) | (SEQ ID NO: 51) |
| GYGYGYGYNYAYK(PNA(A)) | (SEQ ID NO: 52) |
| DYGYYEYEK(PNA(A)). | (SEQ ID NO: 53) |

According to another feature, J is the amino acid G and G is at a terminal end of the peptide moiety. It may be an endogenous amino acid or an added amino acid.

A preferred embodiment is a compound having a formula selected from:

| | |
|---|---|
| KYGVYGFYGNG(PNA(A)) | (SEQ ID NO: 54) |
| SYYHYG(PNA(A)) | (SEQ ID NO: 55) |
| HYGYSYG(PNA(A)) | (SEQ ID NO: 56) |
| AYSYGYNYYGYSG(PNA(A)) | (SEQ ID NO: 57) |
| NYGYGYDYYDYSG(PNA(A)) | (SEQ ID NO: 58) |
| KYGYGYNYYDYSG(PNA(A)) | (SEQ ID NO: 59) |
| GYGYGYGYNYAYG(PNA(A)) | (SEQ ID NO: 60) |
| DYGYYEYEG(PNA(A)). | (SEQ ID NO: 61) |

According to another feature, in $R_1$ and $R_2$ the alkyl is a straight chain hydrocarbon of 1 to 5, preferably 1 to 3, more preferably 1 or 2 carbon atoms.

According to another feature, in Formula (XLI), $R_1$ is —$CH_2CH_2NH_2$.

According to another feature, in Formula (XLI), $R_2$ is —$CH_2C(O)OH$.

According to another feature, in Formula (XLI), $R_1$ is —$CH_2CH_2NH_2$ and $R_2$ is —$CH_2C(O)OH$.

According to another feature, $R_2$ is an alkyl substituted with a group selected from: —C(O)O~, —C(O)~, —C(O)R'~, where R' is alkyl or H, —O~ and —NH~; wherein ~ represents the bond attaching PNA(A) to the amino acid residue J.

Unless defined otherwise, all technical and scientific terms used herein have the same meaning as commonly understood by one of ordinary skill in the art to which this invention belongs.

The term "interfere with," as used herein, means to reduce or inhibit.

The term "naturally-occurring," as used herein with reference to an object, such as a protein, peptide or amino acid, indicates that the object can be found in nature. For example, a protein, peptide or amino acid that is present in an organism or that can be isolated from a source in nature and which has not been intentionally modified by man in the laboratory is considered to be naturally-occurring.

The term "amino acid residue," as used herein, encompasses both naturally-occurring amino acids and non-naturally-occurring amino acids. Examples of non-naturally occurring amino acids include, but are not limited to, D-amino acids (i.e. an amino acid of an opposite chirality to the naturally-occurring form), N-α-methyl amino acids, C-α-methyl amino acids, β-methyl amino acids and D- or L-β-amino acids. Other non-naturally occurring amino acids include, for example, β-alanine (β-Ala), norleucine (Nle), norvaline (Nva), homoarginine (Har), 4-aminobutyric acid (γ-Abu), 2-aminoisobutyric acid (Aib), 6-aminohexanoic acid (ε-Ahx), ornithine (orn), sarcosine, α-amino isobutyric acid, 3-aminopropionic acid, 2,3-diaminopropionic acid (2,3-diaP), D- or L-phenylglycine, D-(trifluoromethyl)-phenylalanine, and D-p-fluorophenylalanine.

A peptide moiety comprising, consisting essentially of, or consisting of, the peptide sequence of a tyrosine cluster YC of the BY-kinase of a bacteria, or a fragment or an analogue thereof, has whole or part of the amino acid sequence of the cluster or have an amino acid sequence which may contain non-naturally-occurring amino acid residues and/or the PNA (A). Preferably, the peptide moiety matches the amino acid sequence of the cluster or of the selected part of the cluster. The term "analogue" indicates that there can be some amino acid residue changes which do not affect substantially the YC function or even may increase the affinity. The term "fragment" means a fragment of the YC wherein the number of amino acid residues is preferably of at least 4 amino acids residues, for example between 4 and 21, preferably 5 and 15 residues.

The term "endogenous" used with amino acid residue means that the amino acid residue is present in the native sequence of the YC.

The term "added" used with amino acid residue means that the amino acid residue is exogenous to the native sequence, i.e. is added or inserted.

As used herein, "peptide bond" can be a naturally-occurring peptide bond or a non-naturally occurring (i.e. modified) peptide bond. Examples of suitable modified peptide bonds are well known in the art and include, but are not limited to, —$CH_2NH$—, —$CH_2S$—, —$CH_2CH_2$—, —CH═CH— (cis or trans), —$COCH_2$—, —$CH(OH)CH_2$—, —$CH_2SO$—, —CS—NH— and —NH—CO— (i.e. a reversed peptide bond) (see, for example, Spatola, Vega Data Vol. 1, Issue 3, (1983); Spatola, in *Chemistry and Biochemistry of Amino Acids Peptides and Proteins*, Weinstein, ed., Marcel Dekker, New York, p. 267 (1983); Morley, J. S., *Trends Pharm. Sci.* pp. 463-468 (1980); Hudson et al., *Int. J. Pept. Prot. Res.* 14:177-185 (1979); Spatola et al., *Life Sci.* 38:1243-1249 (1986); Hann, *J. Chem. Soc. Perkin Trans. I* 307-314 (1982); Almquist et al., *J. Med. Chem.* 23:1392-1398 (1980); Jennings-White et al., *Tetrahedron Lett.* 23:2533 (1982); Szelke et al., EP 45665 (1982); Holladay et al., *Tetrahedron Lett.* 24:4401-4404 (1983); and Hruby, *Life Sci.* 31:189-199 (1982)).

The term "alkyl," as used herein, refers to a straight chain or branched hydrocarbon of one to ten carbon atoms or a cyclic hydrocarbon group of three to ten carbon atoms. Said alkyl group is optionally substituted with one or more substituents independently selected from the group of: alkyl, alkenyl, alkynyl, aryl, heteroalkyl, aralkyl, hydroxy, alkoxy, aralkyloxy, aryloxy, carboxy, acyl, aroyl, halo, nitro, trihalomethyl, cyano, alkoxycarbonyl, aryloxycarbonyl, aralkoxycarbonyl, acylamino, aroylamino, dialkylamino, carbamoyl, alkylcarbamoyl, dialkylcarbamoyl, alkylthio, aralkylthio, arylthio, alkylene and $NZ_1Z_2$ where $Z_1$ and $Z_2$ are independently hydrogen, alkyl, aryl, and aralkyl. This term is exemplified by such groups as methyl, ethyl, n-propyl, i-propyl, n-butyl, t-butyl, l-butyl (or 2-methylpropyl), cyclopropylmethyl, i-amyl, n-amyl, hexyl, cyclopropyl, cyclobutyl, cyclopentyl, and the like.

The term "alkenyl" refers to a straight chain or branched hydrocarbon of two to ten carbon atoms having at least one carbon to carbon double bond. Said alkenyl group can be optionally substituted with one or more substituents as defined above. Exemplary groups include allyl and vinyl.

The term "alkynyl" refers to a straight chain or branched hydrocarbon of two to ten carbon atoms having at least one carbon to carbon triple bond. Said alkynyl group can be optionally substituted with one or more substituents as defined above. Exemplary groups include ethynyl and propargyl.

The term "heteroalkyl," as used herein, refers to an alkyl group of 2 to 10 carbon atoms, wherein at least one carbon is replaced with a hetero atom, such as N, O or S.

The term "aryl" (or "Ar"), as used herein, refers to an aromatic carbocyclic group containing about 6 to about 10 carbon atoms or multiple condensed rings in which at least one ring is aromatic carbocyclic group containing 6 to about 10 carbon atoms. Said aryl or Ar group can be optionally substituted with one or more substituents as defined above. Exemplary aryl groups include phenyl, tolyl, xylyl, biphenyl, naphthyl, 1,2,3,4-tetrahydronaphthyl, anthryl, phenanthryl, 9-fluorenyl, and the like.

The term "aralkyl," as used herein, refers to a straight or branched chain alkyl, alkenyl or alkynyl group, wherein at least one of the hydrogen atoms is replaced with an aryl group, wherein the aryl group can be optionally substituted with one or more substituents as defined above. Exemplary aralkyl group include benzyl, 4-phenylbutyl, 3,3-diphenylpropyl and the like.

The term "alkoxy," as used herein, refers to RO—, wherein R is alkyl, alkenyl or alkynyl in which the alkyl, alkenyl and alkynyl groups are as previously described. Exemplary alkoxy groups include methoxy, ethoxy, n-propoxy, l-propoxy, n-butoxy, and heptoxy.

The term "aryloxy" as used herein, refers to an "aryl-O—" group in which the aryl group is as previously described. Exemplary aryloxy groups include phenoxy and naphthoxy.

The term "alkylthio," as used herein, refers to RS—, wherein R is alkyl, alkenyl or alkynyl in which the alkyl, alkenyl and alkynyl groups are as previously described. Exemplary alkylthio groups include methylthio, ethylthio, l-propylthio and hepthylthio.

The term "arylthio," as used herein, refers to an "aryl-S—" group in which the aryl group is as previously described. Exemplary arylthio groups include phenylthio and naphthylthio.

The term "aralkyloxy," as used herein, refers to an "aralkyl-O—" group in which the aralkyl group is as previously described. Exemplary aralkyloxy groups include benzyloxy.

The term "aralkylthio," as used herein, refers to an "aralkyl-S—" group in which the aralkyl group is as previously described. Exemplary aralkylthio groups include benzylthio.

The term "dialkylamino," as used herein, refers to an —$NZ_1Z_2$ group wherein $Z_1$ and $Z_2$ are independently selected from alkyl, alkenyl or alkynyl, wherein alkyl, alkenyl and alkynyl are as previously described. Exemplary dialkylamino groups include ethylmethylamino, dimethylamino and diethylamino.

The term "alkoxycarbonyl," as used herein, refers to R—O—CO—, wherein R is alkyl, alkenyl or alkynyl, wherein alkyl, alkenyl and alkynyl are as previously described. Exemplary alkoxycarbonyl groups include methoxy-carbonyl and ethoxy-carbonyl.

The term "aryloxycarbonyl," as used herein, refers to an "aryl-O—CO—", wherein aryl is as defined previously. Exemplary aryloxycarbonyl groups include phenoxy-carbonyl and naphtoxy-carbonyl.

The term "aralkoxycarbonyl," as used herein, refers to an "aralkyl-O—CO—," wherein aralkyl is as defined previously. Exemplary aralkoxycarbonyl groups include benzyloxycarbonyl.

The term "acyl" as used herein, refers to RC(O)—, wherein R is alkyl, alkenyl, alkynyl, heteroalkyl, a heterocyclic ring, or a heteroaromatic ring, wherein alkyl, alkenyl, alkynyl, heteroalkyl, heterocyclic, and heteroaromatic are as defined previously.

The term "aroyl" as used herein, refers to an ArC(O)— group, wherein Ar is as defined previously.

The term "carboxy" as used herein, refers to ROC(O)—, wherein R is H, alkyl, alkenyl or alkynyl, and wherein alkyl, alkenyl or alkynyl are as defined previously.

The term "carbamoyl," as used herein, refers to a $H_2N$—CO— group.

The term "alkylcarbamoyl," as used herein, refers to an "$Z_1Z_2N$—CO—" group wherein one of the $Z_1$ and $Z_2$ is hydrogen and the other of $Z_1$ and $Z_2$ is independently selected from alkyl, alkenyl or alkynyl and wherein alkyl, alkenyl and alkynyl are as defined previously.

The term "dialkylcarbamoyl," as used herein, refers to a "$Z_1Z_2N$—CO—" group wherein $Z_1$ and $Z_2$ are independently selected from alkyl, alkenyl or alkynyl and wherein alkyl, alkenyl and alkynyl are as defined previously.

The term "acylamino", as used herein, refers to an "acyl-NH—" group, wherein acyl is as defined previously.

The term "halo" as used herein, refers to fluoro, chloro, bromo or iodo. In one embodiment, "halo" refers to fluoro, chloro or bromo.

Other chemistry terms herein are used according to conventional usage in the art, as exemplified by The McGraw-Hill Dictionary of Chemical Terms (ed. Parker, S., 1985), McGraw-Hill, San Francisco).

The term "reactive functionality," as used herein, refers to a chemical group present on a first molecule that is capable of bonding to, or can be modified and/or activated to be capable of bonding to, a second molecule.

The term "subject" or "patient" as used herein refers to an animal or human in need of treatment or prevention. Human is the main target.

Administration of the inhibitors of the invention "in combination with" one or more further therapeutic agents, is provided for and may include simultaneous (concurrent) administration and consecutive administration. Consecutive administration is intended to encompass administration of the therapeutic agents to the subject in various orders and via various routes.

As used herein, the term "about" refers to a +/−10% variation from the nominal value. It is to be understood that such a variation is always included in any given value provided herein, whether or not it is specifically referred to.

Naturally-occurring amino acids are identified throughout by the conventional three-letter or one-letter abbreviations indicated below, which are as generally accepted in the peptide art and are recommended by the IUPAC-IUB commission in biochemical nomenclature:

TABLE 1

Amino acid codes

| Name | 3-letter code | 1-letter code |
|---|---|---|
| Alanine | Ala | A |
| Arginine | Arg | R |
| Asparagine | Asn | N |
| Aspartic | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The peptide sequences set out herein are written according to the generally accepted convention whereby the N-terminal amino acid is on the left and the C-terminal amino acid is on the right.

In accordance with another aspect of the present invention, there is provided a pharmaceutical composition or drug comprising a compound as defined herein and a pharmaceutically acceptable diluent, carrier or excipient. This compound may act as a BY-kinase inhibitor.

According to a feature, the pharmaceutical composition or drug (medicament) of the invention comprises at least two such compounds each having a peptide moiety comprising, consisting essentially of, or consisting of, the peptide sequence of a naturally-occurring tyrosine cluster of the BY-kinase, or a fragment or an analogue thereof, of at least two different bacteriae.

According to different embodiments, the pharmaceutical composition or drug comprises one or several (2 or more) inhibitory compounds directed against one of the following bacteriae:
Streptococcus pneumoniae
Staphylococcus aureus
Escherichia coli:

*Erwinia* species (*amylovora, carotovora, stewartii, chrysanthemi* . . . )
*Klebsiella pneumoniae*
*Acinetobacter* species (*calcoaceticus, baumannii, johnsonii* . . . )
*Pseudomonas* (*Rastonia*) *solanacearum*
*Shigella* species (*flexneri, boydii, sonnei, dysenteriae*)
*Salmonella typhi*
*Vibrio cholerae.*

In accordance with another aspect of the present invention, there is provided an inhibitor compound or pharmaceutical composition or drug of the invention for use in the treatment of a bacterial infection or in the prevention of a bacterial infection.

According to a feature, the pharmaceutical composition or drug of the invention comprises at least two such compounds each having a peptide moiety comprising, consisting essentially of, or consisting of, the peptide sequence of a naturally-occurring tyrosine cluster of the BY-kinase, or a fragment or an analogue thereof, of at least two different bacteriae.

In accordance with another aspect of the present invention, there is provided a use of such an inhibitor compound of the invention for the manufacture of a drug for use in the treatment of a bacterial infection or in the prevention of a bacterial infection.

According to a feature, the pharmaceutical composition or drug of the invention comprises at least two such compounds each having a peptide moiety comprising, consisting essentially of, or consisting of, the peptide sequence of a naturally-occurring tyrosine cluster of the BY-kinase, or a fragment or an analogue thereof, of at least two different bacteriae.

In accordance with another aspect of the present invention, there is provided a method of treating a subject against bacterial infection comprising administering to said subject an effective amount of a compound inhibitor, pharmaceutical composition or drug of the invention.

In accordance with another aspect of the present invention, there is provided a method of preventing bacterial infection by a subject comprising administering to said subject an effective amount of a compound inhibitor, pharmaceutical composition or drug of the invention.

According to a feature, the pharmaceutical composition or drug of the invention comprises at least two such compounds each having a peptide moiety comprising, consisting essentially of, or consisting of, the peptide sequence of a naturally-occurring tyrosine cluster of the BY-kinase, or a fragment or an analogue thereof, of at least two different bacteriae.

According to different embodiments, in the method or use according to the invention, pharmaceutical compositions or drugs are used which comprises one or several (2 or more) inhibitory compounds directed against one of the following bacteriae:
*Streptococcus pneumoniae*
*Staphylococcus aureus*
*Escherichia coli:*
*Erwinia* species (*amylovora, carotovora, stewartii, chrysanthemi* . . . )
*Klebsiella pneumoniae*
*Acinetobacter* species (*calcoaceticus, baumannii, johnsonii* . . . )
*Pseudomonas* (*Rastonia*) *solanacearum*
*Shigella* species (*flexneri, boydii, sonnei, dysenteriae*)
*Salmonella typhi*
*Vibrio cholerae.*

In the method and use of the invention, when several compounds are chosen to be administered to the same subject, they can be in the same pharmaceutical composition or drug, or in separate ones.

The inhibitory compounds of the present invention can be prepared using standard synthetic techniques known in the art. The components of the inhibitors can be prepared sequentially, concurrently or as part of a single process. For example, the peptide moiety can be synthesized and then conjugated using standard conjugation chemistry techniques to the PNA (A) molecule, which can either have been synthesized separately or obtained from commercial sources. Alternatively, the peptide moiety and the PNA(A) can be synthesized together as a single molecule.

The peptide moiety can be readily prepared by standard peptide synthesis techniques known in the art, for example, by standard solution, suspension or solid phase techniques, such as exclusive solid phase synthesis, partial solid phase synthesis methods, fragment condensation and classical solution synthesis.

In one embodiment of the present invention, solid phase techniques are employed to prepare the peptide moiety. The principles of solid phase chemical synthesis of peptides are well known in the art and may be found in general texts in the area such as Pennington, M. W. and Dunn, B. M., *Methods in Molecular Biology*, Vol. 35 (Humana Press, 1994); Dugas, H. and Penney, C., *Bioorganic Chemistry* (1981) Springer-Verlag, New York, pgs. 54-92; Merrifield, J. M., *Chem. Soc.*, 85:2149 (1962), and Stewart and Young, *Solid Phase Peptide Synthesis*, pp. 24-66, Freeman (San Francisco, 1969).

An insoluble polymer support (or resin) is used to prepare the starting material by attaching a protected version of the required α-amino acid to the resin. The resin acts to anchor the peptide chain as each additional α-amino acid is attached and is composed of particles (generally between about 20-50 μm diameter) that are chemically inert to the reagents and solvents used in solid phase peptide synthesis. These particles swell extensively in solvents, which makes the linker arms more accessible. Examples of resins used in solid phase peptide synthesis include chloromethylated resins, hydroxymethyl resins, benzhydrylamine resins, and the like. Various resins suitable for solid phase peptide synthesis applications are available commercially, for example, phenylacetamidomethyl (PAM) resin, hydroxymethyl polystyrene-vinylbenzene copolymer, polyamide, p-benzyloxybenzyl alcohol resin (Wang resin) and modified versions thereof, 4-hydroxymethyl phenoxymethyl-copoly(styrene-1% divinylbenzene), and 4-(2',4'-dimethoxyphenyl-Fmoc-aminomethyl)phenoxyacetamidoethyl and [5-(4-Fmoc-aminomethyl-3,5-dimethoxyphenoxy)valeric acid]-polyethylene glycol-polystyrene resins (which are commercially available from Applied Biosystems, Foster City, Calif.) and can be used in the preparation of the peptide moiety of the invention.

The α-amino acid is coupled to the resin using a standard coupling reagent such as N,N'-dicyclohexylcarbodiimide (DCC), N,N'-diisopropylcarbodiimide (DIC) or O-benzotriazol-1-yl-N,N, N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl). The coupling generally takes place in a solvent such as dichloromethane, DMF or NMP.

After the initial coupling, the α-amino protecting group is removed using a standard reagent, such as a solution of trifluoroacetic acid (TFA), hydrochloric acid in an organic solvent or 20% piperidine in DMF solvent.

Suitable α-amino protecting groups are known in the art of and include, for example, acyl type protecting groups (such as, formyl, trifluoroacetyl, acetyl), aromatic urethane type protecting groups (such as, benzyloxycarboyl (Cbz) and substituted Cbz), aliphatic urethane protecting groups (such as, t-butyloxycarbonyl (Boc), isopropyloxycarbonyl and cyclohexyloxycarbonyl), alkyl type protecting groups (such as, benzyl and triphenylmethyl) and 9-fluorenylmethoxy carbonyl (Fmoc). A labile group protects the alpha-amino group of the amino acid. This group should be easily removed after each coupling reaction so that the next α-amino protected amino acid may be added.

Side chain protecting groups, when used, remain intact during coupling and typically are not removed during the deprotection of the amino-terminus protecting group or during coupling. Side chain protecting groups are generally selected such that they are removable upon the completion of the synthesis of the final peptide and under reaction conditions that will not alter the peptide. Examples of side chain protecting groups include, but are not limited to, benzyl, 2,6-dichlorobenzyl, methyl, ethyl, and cyclohexyl for Asp; acetyl, benzoyl, trityl, tetrahydropyranyl, benzyl, 2,6-dichlorobenzyl, and Cbz for Ser; nitro, Tosyl (Tos), Cbz, adamantyloxycarbonyl mesitoylsulfonyl (Mts), or Boc for Arg and Cbz, 2-chlorobenzyloxycarbonyl (2-Cl-Cbz), and 2-bromobenzyloxycarbonyl (2-BrCbz), ivDde, Tos, or Boc for Lys. Other examples are known in the art.

After removal of the α-amino protecting group, the remaining protected amino acids are coupled in the desired order to the peptide chain in a stepwise manner. An excess of each protected amino acid is generally used with an appropriate carboxyl group activator, such as dicyclohexylcarbodiimide (DCC) in methylene chloride and/or dimethyl formamide (DMF), N-[(dimethylamino)-1H-1,2,3-triazolo[4,5-b]pyridin-1-ylmethylene]-N-methylmethanaminium hexafluorophosphate N-oxide (HATU), N-[1H-benzotriazol-1-yl)-(dimethylamino)methylene]-N-methylmethanaminium hexafluorophosphate N-oxide (HBTU), and (benzotriazol-1-yl-N-oxy)tris(dimethylamino)phosphonium hexafluorophosphate (BOP).

Once the desired amino acid sequence has been synthesized, the stable blocking groups are removed and the peptide is decoupled from the resin support by treatment with a suitable reagent, such as Reagent K, which includes TFA (82.5%), Thioanisole (5%), Phenol (5%), $H_2O$ (5%), 1,2-ethanedithiol (EDT, 2.5%). The decoupling reagent may simultaneously cleave any side chain protecting groups. Alternatively, the side chain protecting groups can be cleaved off using a separate reagent, for example, 20% piperidine in DMF for Fmoc groups or 2% hydrazine in DMF for ivDde groups.

In one embodiment of the present invention, the peptide moiety is synthesized on a commercially available peptide synthesizer (such as the Pioneer Peptide Synthesizer available from Applied Biosystems, Foster City, Calif., or the Liberty System from CEM Corporation, Matthews, N.C.) following the manufacturer's instructions and employing suitable protecting groups to protect the amino acid side chains, as necessary.

The above techniques can also be used to synthesize peptide moieties which include one or more non-naturally occurring amino acids. Covalent modifications can be introduced, for example, by reacting targeted amino acid residues with an organic derivatising agent that is capable of reacting with selected amino acid side chains or with the terminal residue(s) as is known in the art. Selection of appropriate derivatising agent(s) can be readily accomplished by a worker skilled in the art.

Methods of synthesizing peptides having one or more modified peptide bonds are known in the art (see, for example, "Solid Phase Peptide Synthesis" *Methods in Enzymology* (ed. Fields, G. B. (1997) Academic Press, San Diego).

The peptide moiety can also be prepared in their salt form. The peptides may be sufficiently acidic or sufficiently basic to react with a number of inorganic bases, inorganic acids or organic acids, to form a salt. Acids commonly employed to form acid addition salts are inorganic acids such as hydrochloric acid, hydrobromic acid, hydroiodic acid, sulphuric acid, phosphoric acid, and the like, and organic acids such as p-toluenesulphonic acid, methanesulphonic acid, oxalic acid, p-bromophenyl-sulphonic acid, carbonic acid, succinic acid, citric acid, benzoic acid, acetic acid, and the like.

Base addition salts include those derived from inorganic bases, such as ammonium or alkali or alkaline earth metal hydroxides, carbonates, bicarbonates, and the like. Examples of bases useful in preparing the salts include, but are not limited to, sodium hydroxide, potassium hydroxide, ammonium hydroxide, potassium carbonate, and the like.

The present invention also contemplates that when the peptide moiety comprises naturally occurring amino acids or slightly modified versions thereof, they can be prepared by recombinant DNA techniques. Such methods can be found generally described in Ausubel et al. (*Current Protocols in Molecular Biology*, Wiley & Sons, NY (1997 and updates)) and Sambrook et al. (*Molecular Cloning: A Laboratory Manual*, Cold-Spring Harbor Press, NY (2001)). In general, a DNA sequence encoding the peptide moiety is prepared and inserted into a suitable expression vector. The expression vector is subsequently introduced into a suitable host cell or tissue by one of a variety of methods known in the art, for example, by stable or transient transfection, lipofection, electroporation, or infection with a recombinant viral vector. The host cell or tissue is cultured under conditions that allow for the expression of the peptide moiety and the latter is subsequently isolated from the cells/tissue.

Examples of suitable expression vectors include, but are not limited to, plasmids, phagemids, cosmids, bacteriophages, baculoviruses and retroviruses, and DNA viruses. The selected expression vector can further include one or more regulatory elements to facilitate expression of the peptide moiety, for example, promoters, enhancers, terminators, and polyadenylation signals. One skilled in the art will appreciate that such regulatory elements may be derived from a variety of sources, including bacterial, fungal, viral, mammalian or insect genes.

In the context of the present invention, the expression vector may additionally contain heterologous nucleic acid sequences that facilitate the purification of the expressed peptide moiety. Examples of such heterologous nucleic acid sequences include, but are not limited to, affinity tags such as metal-affinity tags, histidine tags, avidin/strepavidin encoding sequences, glutathione-S-transferase (GST) encoding sequences and biotin encoding sequences.

One skilled in the art will understand that selection of the appropriate host cell for expression of the recombinant peptide moiety will be dependent upon the vector chosen. Examples of suitable host cells include, but are not limited to, bacterial, yeast, insect, plant and mammalian cells.

If the peptide moiety cannot be encoded or expressed but are very similar to a peptide that can be encoded or expressed, genetic engineering techniques such as those described above can be employed to prepare the encodable peptide, followed by one or more steps in which the encoded peptide is modified by chemical or enzymatic techniques to prepare the final peptide moiety.

Standard conjugation techniques known in the art can be employed to conjugate the individual components of the compound together (see, for example, Morrison and Boyd, Organic Chemistry, 6th Ed. (Prentice Hall, 1992); J. March, Advanced Organic Chemistry, $4^{th}$ Ed. (Wiley 1992); G. T. Harmanson, Bioconjugate Techniques, (Academic Press, Inc. 1995), and S. S. Wong, Chemistry of Protein Conjugation and Cross-Linking, (CRC Press, Inc. 1991)).

The components are conjugated through a reactive functionality on one or more of the components either directly or by modification of the group to introduce a new chemical group capable of conjugating a second component. A variety of chemical groups can be subject to conjugation reactions. For example, hydroxyl groups (—OH) can be used to conjugate a second component through reaction with alkyl halides (R—Cl, R—Br), acyl anhydrides, acyl halides, aldehydes (—CHO), hydrazides (R—CO—NH—NH$_2$), and the like. Primary amino groups (—NH$_2$) can be used to conjugate a second component through reaction with alkyl halides (R—Cl, R—Br, R—I), aryl azides, acyl anhydrides, acyl halides, acyl esters, carboxylates activated with carbodiimides, aldehydes (—CHO), and the like. Carboxylic groups (—COOH) can also be used to conjugate a second component after the group has been activated. Suitable activation agents include, for example, organic or inorganic acid halides (for example pivaloyl chloride, ethyl chloroformate, thionyl chloride, PCl$_5$), carbodiimides (R—CO—OH+R'—N=C=N—R", for example EDC, DCC), benzotriazolyl uronium or phosphonium salts (TBTU, BOP, PyBOP, HTBU), diacyl chlorides, diisocyanates, and the like.

Some of the above reagents can also be used as bifunctional cross-linking reagents that can be employed to conjugate the components of the compound. A variety of such cross-linking reagents is known in the art and many are commercially available (see, for example, S. S. Wong, ibid., and catalogues from Pierce Chemical Co. and Sigma-Aldrich). Examples include, but are not limited to, diamines, such as 1,6-diaminohexane; dialdehydes, such as glutaraldehyde; bis-N-hydroxysuccinimide esters, such as ethylene glycol-bis(succinic acid N-hydroxysuccinimide ester), disuccinimidyl glutarate, disuccinimidyl suberate, and ethylene glycol-bis (succinimidylsuccinate); diisocyantes, such as hexamethylenediisocyanate; bis oxiranes, such as 1,4 butanediyl diglycidyl ether; dicarboxylic acids, such as succinyldisalicylate; 3-maleimidopropionic acid N-hydroxysuccinimide ester, and the like.

Prior to conjugation, one or more of the components of the compound can be submitted to one or more purification procedures, as can the final compound. Purification methods are well known in the art (see, for example, T. Hanai, HPLC: A Practical Guide, RSC Press, UK 1999; L. M. Harwood, C. J. Moody and J. M. Percy, Experimental Organic Chemistry: Standard and Microscale, Blackwell Scientific Publishing, 1998; Current Protocols in Protein Science, Coligan, J. E., et al. (eds.), John Wiley & Sons, (2001 & updates)) and can include one or more chromatographic steps, for example, ion exchange chromatography, hydrophobic adsorption/interaction chromatography, silica gel adsorption chromatography, and various forms of high performance liquid chromatography (HPLC), such as reverse-phase HPLC.

EXAMPLE 1

To assess the inhibitory effect of a potential drug onto a BY-kinase, two distinct procedures are used, each one being an object of the invention. Procedure 1 is based on the detection of the autokinase activity of a BY-kinase in the presence or in the absence of the drug to be tested. In the Procedure 2, the ability of a BY-kinase to phosphorylate an endogenous protein substrate in the presence or in the absence of the drug is measured. A drug is considered as efficient when either the autokinase or the kinase activities, or both activities, is/are affected.

To perform Procedure 1 and Procedure 2, the BY-kinase and the protein substrate of interest are first purified to homogeneity. For this, each corresponding gene is amplified by PCR and cloned into an overexpressing vector. Each protein is fused to a tag (6 histidines, GlutathionS-tranferase, etc.) allowing its purification to near homogeneity in a single step. The bacterial strains and the growth conditions used to overproduce the protein of interest are chosen to satisfy quantity and solubility criteria. Purification is then achieved by chromatographic techniques based on the affinity of a matrix for the tag fused to the protein of interest. After elution and salting-out, proteins of interest are ready for the inhibitory tests. Alternatively, they are stored at 4° C. to −80° C. and tested later.

The inhibitory effect of a drug is tested either directly after purification, or after a subsequent step of dephosphorylation (see §Dephosphorylation).

The effect of a drug, after performing procedure 1 and/or 2, may be analyzed by three different methods (see §Analysis)

Dephosphorylation

When appropriate, the purified BY-kinase of interest is dephosphorylated as follows. 1 to 10 U of alcalin phosphatase per 30 pmole of BY-kinase is mixed and incubated for 15 min to 10 hours at 25° C. to 42° C. in the appropriate buffer provided by the manufacturer. The maximum final volume should not exceed 2 ml.

After dephosphorylation, the mixture is buffered appropriately so as to obtain the pH condition allowing purification again of the dephosphorylated BY-kinase using the same chromatographic method that has led to its purification from the overproducing bacterial strain. After salting out, the dephosphorylated BY-kinase is considered ready to use for inhibitory tests. Alternatively, it is stored at 4° C. to −80° C. and tested later.

Procedure 1: Effect of a Potential Drug on the Autokinase Activity of a BY-kinase 50 pmole of the purified BY-kinase (or the dephosphorylated BY-kinase) are incubated for 15 min to 1 hour in the presence of 50 pmole of the drug in a final volume of 20 microliters. The ratio BY-kinase/drug varies from 1/1 to 1/100. The reaction is performed in a buffer specific of each BY-kinase (pH condition, salt concentrations, etc.). The incubation is then continued for 30" to 1 h in the presence of 5 microCurie of radioactive ATP ($^{32}$P or $^{33}$P) labeled on g-P (specific activity 3000 Ci/mmole) and 50 microMolar non-radioactive ATP. The reaction is stopped by adding 5 microliter of gel-electrophoresis loading buffer 5 fold concentrate and heating 5 min at 100° C. The radioactivity bound to the BY-kinase and corresponding to the ability of the enzyme to be phosphorylated is measured as described in §Analysis to determine the potential inhibitory effect of the studied drug.

Procedure 2: Ability of a BY-kinase to Phosphorylate an Endogenous Protein Substrate in the Presence or in the Absence of the Potential Drug The procedure 2 is based on procedure 1, except that 5 pmole to 100 pmole of the protein substrate are also added either in the same time as the drug or concomitant with the radioactive ATP and the non-radioactive ATP. The potential inhibitory effect of the studied drug is determined as described in §Analysis by measuring the radioactivity bound to the protein substrate.

Analysis

Drugs tested as described in Procedure 1 or 2 are analyzed for their inhibitory power by the three methods indicated here below. The phosphorylation signal of a BY-kinase (Procedure 1) or a protein substrate (Procedure 2) incubated with the drug is compared to BY-kinase or protein substrate signals obtained in the same condition but incubated in the absence of the drug. Any decrease of the phosphorylation signal by one of the 3 methods indicates that the autokinase or the kinase activity of a BY-kinase is affected by the drug, which therefore has an inhibitory effect.

Method 1

Samples are analyzed by SDS-PAGE. After electrophoresis, gels are soaked in 16% (w/v) trichloroacetic acid for ten minutes at 90° C. They are stained with 0.1% (w/v) Coomassie blue R-250 in 50% (v/v) ethanol, 7.5% (v/v) acetic acid, and dried under vacuum. Radioactive bands are visualized by autoradiography using direct exposure films.

Method 2

Method 2 is based on Method 1, except that samples are analyzed on native polyacrylamide electrophoresis gel without SDS. In addition to direct film exposure, the autokinase activity or the protein substrate phosphorylation is analyzed by detecting the apparition of stained (Coomassie-blue- or silver-) phosphorylated forms of the BY-kinase or the protein substrate.

Method 3

Samples are analyzed by either SDS polyacrylamide gel electrophoresis (method 1) or native polyacrylamide electrophoresis gel without SDS (method 2). Then, they are electrotransfered onto an Immobilon polyvinylidene difluoride (PVDF) membrane. Phosphorylation signals are detected by immunoblotting by using PY20 (Sigma) or 4G10 (upstate) monoclonal anti-phosphotyrosine-HRP conjugate.

Method 2 and Method 3 may also be performed with radioactive ATP so as to detect phosphorylated proteins with specific anti-phosphotyrosine antibody (see §analysis).

EXAMPLE

Procedure for the Inhibition Test of the BY-kinase A1B2 from *Staphylococcus aureus* with the Drug BYK001 (See Example 2)

The procedure was applied for A1B2 [34] and CapO [20] Each Gene has been cloned in the pQE30 vector (Qiagen) to allow fusion of a histidines-tag fused to the N-terminal end of either A1B2 or CapO. This overproducing plasmid has been transformed in the *Escherichia coli* XL 1-blue strain. Cells have been incubated at 37° C. under shaking until A600 reached 0.5. IPTG was then added at a final concentration of 0.5 mM, and growth was continued for 3 h at 37° C. under shaking. Cells were harvested by centrifugation at 3000×g for 10 min, washed in buffer A (Tris-HCl 50 mM pH7.5, Nacl 200 mM, glycerol 10%, imidazole 10 mM) containing DNase I and RNase A at a final concentration of 5 mg/ml each, lysozyme 1 mg/ml, and protease inhibitors cocktail. Cells were disrupted by sonication. The resulting suspension was centrifuged at 4° C. for 30 min at 30,000×g. The supernatant was incubated with Ni-NTA matrix (Qiagen), suitable for purification of 6 histidines fusion proteins, for 30 min at 4° C. under gentle shaking. The protein-resin complex was packed into a column for washing and elution steps. The column was washed with buffer B (Tris-HCl 50 mM pH7.5, Nacl 200 mM, glycerol 10%, imidazole 20 mM). Protein elution was carried out with buffer C (Tris-HCl 50 mM pH7.5, NaCl 200 mM, glycerol 10%, imidazole 150 mM). Eluted fractions were collected, analyzed by SDS-PAGE. Appropriated fractions are pooled and dialyzed overnight against buffer D (Tris-HCl 50 mM, pH7.5, NaCl 100 mM, DTT 1 mM, MgCl2 1 mM, glycerol 20%) and used for inhibitory tests or stored at +4° C., −20° C., or −80° C.

According to procedure 1, 50 pmole of A1B2 were incubated with either, 0 pmole, 50 pmole, or 500 pmole, or 5 nmol of BYK001 for 15 min at 37° C. in a final volume of 20 ml. Then, incubation was continued for 30", or 1', or 2' or 5' in the presence of 5 mCi of [g-$^{32}$P] ATP (specific activity 3000 Ci/mmole). The amount of radioactivity incorporated in A1B2 was determined by fluid scintillation counting after gel-electophoresis. The percentage of inhibition of A1B2 autokinase activity is expressed relatively to the radioactivity incorporated in A1B2 when incubated without BYK001.

Results are presented in the table in Table 2:

|  | BYK001 (pmole) | | | | | | | |
|---|---|---|---|---|---|---|---|---|
|  | 0 | | | | 50 | | | |
| Incubation time (min) | 0.5 | 1 | 2 | 5 | 0.5 | 1 | 2 | 5 |
| Radioactivity incorporated in A1B2 (cpm) | 35453 | 85435 | 158973 | 381765 | 29233 | 71683 | 132537 | 325711 |
| % of inhibition | 0 | 0 | 0 | 0 | 17.54 | 16.10 | 16.63 | 14.68 |
|  | BYK001 (pmole) | | | | | | | |
|  | 500 | | | | 5000 | | | |
| Incubation time (min) | 0.5 | 1 | 2 | 5 | 0.5 | 1 | 2 | 5 |
| Radioactivity incorporated in A1B2 (cpm) | 30734 | 72475 | 133624 | 324983 | 29899 | 72528 | 141005 | 323749 |
| % of inhibition | 13.31 | 15.17 | 15.95 | 14.87 | 15.67 | 15.11 | 11.30 | 15.20 |

According to procedure 2, 50 pmol of A1B2 and 50 pmole of a substrate of A1B2, namely the protein CapO, were incubated with either 50 pmole, or 500 pmole, or 5 nmol of BYK001 for 15 min at 37° C. in a final volume of 20 ml. Then, incubation was continued for 30", or 1', or 2' or 5' in the presence of 5 mCi of [g-$^{32}$P] ATP (specific activity 3000 Ci/mmole). The amount of radioactivity incorporated in CapO was determined by fluid scintillation counting after gel-electophoresis. The percentage of inhibition of CapO phosphorylation by A1B2 is expressed relatively to CapO radioactivity when incubation was performed without BYK001.

Results are presented in the table in Table 3:

|  | BYK001 (pmole) | | | | | | | |
|---|---|---|---|---|---|---|---|---|
|  | 0 | | | | 50 | | | |
| Incubation time (min) | 0.5 | 1 | 2 | 5 | 0.5 | 1 | 2 | 5 |
| Radioactivity incorporated in CapO(cpm) | 3952 | 7045 | 17354 | 34718 | 3555 | 6388 | 15498 | 31901 |
| % of inhibition | 0 | 0 | 0 | 0 | 10.05 | 9.33 | 10.69 | 8.11 |
|  | BYK001 (pmole) | | | | | | | |
|  | 500 | | | | 5000 | | | |
| Incubation time (min) | 0.5 | 1 | 2 | 5 | 0.5 | 1 | 2 | 5 |
| Radioactivity incorporated in CapO(cpm) | 3497 | 6302 | 15549 | 31251 | 3513 | 6315 | 15471 | 30974 |
| % of inhibition | 11.51 | 10.55 | 10.40 | 9.99 | 11.11 | 10.36 | 10.85 | 10.78 |

Results demonstrate an inhibitory effect for BYK001 on BY-kinase A1B2 from *Staphylococcus aureus*.

EXAMPLE 2

In Silico Designing of Analogues from BYK001

Interaction analysis between the tyrosine cluster and the protein kinases was performed. This analysis was carried out with sybyl molecular modelling package (Tripos Inc.) on a Linux workstation. The energy of interaction was computed between the tyrosine cluster and the protein kinase using molecular mechanics with the forcefield Tripos and partials charges of atoms of the structure were computed with the "marsilli gasteiger" algorithm.

The tyrosine cluster was mutated with a lysine and a PNA moiety bonded on its side chain. The global structure was energetically optimized. The energy of interaction was computed and was used as etalon for the other compounds. An investigation was performed for each amino acid of the tyrosine cluster. After checking the interaction for the kinases the amino acid was mutated to another which has an optimal interaction in term of hydrogen bond or hydrophobic interaction in order to optimize the compound. Several strategies were applied to create BYK002-7. See table 4 below with the formula of these compounds and on the line below each formula, the correspondence with the letters of Formula (I).

| name | Sequence | | | | | | | | | | |
|---|---|---|---|---|---|---|---|---|---|---|---|
|  | 1 | 2 | 3 | 4 | 5 | 6 | 7 | 8 | 9 | 10 | 11 |
| BYK001 | S | A | S | Y | Y U | A X | Y Y | K(PNA) Z | G | T | D |
| BYK002 | E | S | S | Y | G U | A X | Y Y | K(PNA) Z | G | T | D |
| BYK003 | K | H | S | E | Y U | G X | Y Y | K(PNA) Z | G | T | K |
| BYK004 | Y U | N X | Y Y | Y U | G X | Y Y | S U | K(PNA) Z | S | E | K |
| BYK005 | K | H | S | E | G U | E X | Y Y | K(PNA) Z | E | T | K U |
| BYK006 | S | S | S | Y | Y U | H X | Y Y | K(PNA) Z | G | D | E |
| BYK007 | V | Y | G | F | Y U | G X | N Y | K(PNA) Z | G | K | K |

The analysis reveals that the native sequence of BYK001 has good interaction energy and that this interaction energy may be increased. The inhibition is around 15% for the BYK001 molecule; according to simulation for interaction Energy, the inhibition percentage is expected to be higher for the analogues (see table 5 below):

|  | Energy | | EnergY | | |
|---|---|---|---|---|---|
|  | kcal·mol−1 | ActivitY | Prot | BYK | Complex |
| BYK001 | −61.9 | 15.00% | 1281.739 | 65.474 | 1285.352 |
| BYK002 | −56.3 |  | 1271.968 | 68.134 | 1283.768 |
| BYK003 | −71.3 |  | 1291.631 | 95.058 | 1315.37 |
| BYK004 | −65.3 |  | 1371.991 | 67.776 | 1374.43 |
| BYK005 | −78.5 |  | 1276.393 | 95.693 | 1293.629 |
| BYK006 | −67.7 |  | 1247.054 | 84.704 | 1264.053 |
| BYK007 | −63.7 |  | 1250.421 | 62.767 | 1249.447 |

REFERENCES

1. Cozzone A J (1988) Annu Rev Microbiol 42: 97-125.
2. Hoch J A (2000) Curr Opin Microbiol 3: 165-170.
3. Deutscher J et al. (2006) Microbiol Mol Biol Rev 70: 939-1031.

4. Kannan N, Neuwald A F (2005) J Mol Biol 351: 956-972.
5. Shi L. et at (1998) FEMS Microbiol Rev 22: 229-253.
6. Macek B et al. (2007) Mol Cell Proteomics 6: 697-707.
7. Macek B et al. (2008) Mol Cell Proteomics 7: 299-307.
8. Lander E S. et al. (2001) Nature 409:860-921.
9. Iyer L M et al. (2004) J Struct Biol 146:11-31.
10. Saraste M et al. (1990) Trends Biochem Sci 15: 430-434.
11. Deutscher J, Saier M H, Jr. (2005) J Mol Microbiol Biotechnol 9:125-131.
12. Fieulaine S et al. (2002) Proc Natl Acad Sci USA 99: 13437-13441.
13. Mijakovic I. et al. (2002) Proc Natl Acad Sci USA 99: 13442-13447.
14. Reizer J et al. (1998) Mol Microbiol 27:1157-1169.
15. Grangeasse C et al. (1997) Gene 204: 259-265.
16. Cozzone A J et al. (2004) Arch Microbiol 181: 171-181.
17. Grangeasse C et al. (2007) Trends Biochem Sci 32: 86-94.
18. Grangeasse C et al. (2003) J Biol Chem 278: 39323-39329.
19. Mijakovic I et al. (2003) Embo J 22: 4709-4718.
20. Soulat D et al. (2007) J Mol Microbiol Biotechnol 13: 45-54.
21. Klein G et al. (2003) Mol Microbiol 48: 269-285.
22. Mijakovic I et al. (2006) Nucleic Acids Res 34:1588-1596.
23. Petranovic D et al. (2007) Mol Microbiol 63: 1797-1805.
24. Whitfield C (2006) Annu Rev Biochem 75: 39-68.
25. Morona R et al. (2000) Microbiology 146 (Pt 1): 1-4.
26. Niemeyer D, Becker A (2001) J Bacteriol 183:5163-5170.
27. Nakar D, Gutnick D L (2003) J Bacteriol 185:1001-1009.
28. Obadia B et al. (2007) J Mol Bio 1367: 42-53.
29. Roberts I S (1996) Annu Rev Microbiol 50:285-315.
30. Thakker M et al. (1998) Infect Immun 66:5183-5189.
31. O'Riordan K, Lee J C (2004) Clin Microbiol Rev 17:218-234.
32. Cunnion K M et al. (2003) Infect Immun 71: 656-662.
33. Karakawa W W et al. (1988) Infect Imun 56: 1090-1095.
34. Olivares-Illana et al. PLoS Biol, (2008) 6, e143.

The invention claimed is:

1. A compound comprising a peptide moiety comprising, the peptide sequence of a tyrosine cluster YC of the BY-kinase of a bacteria, or a fragment or an analogue thereof, and an adenine peptide analogue PNA(A), whereas the peptide moiety and the PNA(A) are linked together.

2. The compound of claim 1, wherein the peptide moiety and the PNA(A) are linked together through a peptide bond.

3. A compound of claim 1, wherein the peptide moiety comprises a sequence as depicted on SEQ ID NO: 1, 2, 3, 4, 5, 6, 7, 8, 9, 10, 11, 12, 13 or 14.

4. A compound of claim 1, wherein the YC is as depicted on SEQ ID NO: 15, 16, 17, 18, 19, 20, 21, 22, 23, 24, 25, 26, 27, 28, 29 or 30.

5. A compound of claim 1, wherein the peptide moiety is as depicted on SEQ ID NO: 15, 16, 17, 18, 19, 20, 21, 22, 23, 24, 25, 26, 27, 28, 29 or 30.

6. A compound of claim 1, wherein the YC is as depicted on SEQ ID NO: 31, 32, 33, 34, 35, 36, 37 or 38.

7. A compound of claim 1, wherein the peptide moiety is as depicted on SEQ ID NO: 31, 32, 33, 34, 35, 36, 37 or 38.

8. The compound of claim 1, wherein the PNA(A) is linked at the C-terminal end of the peptide moiety.

9. The compound of claim 1, wherein the PNA(A) is linked to the peptide moiety through a K or G amino acid residue.

10. The compound of claim 1, wherein the PNA(A) is linked at the C-terminal end of the peptide moiety through a K or G amino acid residue.

11. The compound of claim 1, wherein the compound has a number of amino acid residues between 4 and 21.

12. The compound of claim 1, wherein the PNA(A) is of general formula (XLI):

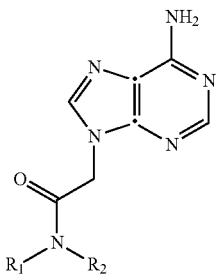

(XLI)

wherein:
$R_1$ and $R_2$ are independently an alkyl substituted with a carboxyl, carbonyl, alcohol or primary amino.

13. The compound of claim 12, comprising a peptide moiety having a sequence selected from the group consisting of:

```
SVDKYGVYGFYGNYGKK,             (SEQ ID NO: 1)
KTKVDKSSSYYHYYGDE,             (SEQ ID NO: 2)
KDKSASYYAYYGTDES,              (SEQ ID NO: 3)
KASSYYRYGHNHYGYSYYDKK,         (SEQ ID NO: 4)
RRASAYQDYGYYEYEYKSDAK,         (SEQ ID NO: 5)
KRASTAYSYGYNYYGYSYSEKE,        (SEQ ID NO: 6)
RRASAYQDYGYYEYEYKSDAK,         (SEQ ID NO: 7)
KSANNYGYGYDYYDYSYQQGEKS,       (SEQ ID NO: 8)
KKATNKYGYGYNYYDYSYSDKK,        (SEQ ID NO: 9)
SSAGYGYGYGY-NYAYAYKANKESD,     (SEQ ID NO: 10)
DPNTYRYGYGSRYGRYRYVQYGYTSNSKPPEAESA, (SEQ ID NO: 11)
RASAYQDYGYYEYEYKSDAK,          (SEQ ID NO: 12)
RATGYQDYGYYEYEYQSDSK,          (SEQ ID NO: 13)
and
KKASRYSGYYHYQAYYGEETKSGAAK.    (SEQ ID NO: 14)
```

14. The compound of claim 12, comprising a peptide moiety having a sequence selected from the group consisting of:

```
DKYGVYGFYGNYGK,                (SEQ ID NO: 15)
SSYYHYYGD,                     (SEQ ID NO: 16)
ASYYAYYGT,                     (SEQ ID NO: 17)
SSYYRYGH,                      (SEQ ID NO: 18)
NHYGYSYYDK,                    (SEQ ID NO: 19)
SAYQDYGYYEYEYKS,               (SEQ ID NO: 20)
TAYSYGYNYYGYSYSE,              (SEQ ID NO: 21)
SAYQDYGYYEYEYKS,               (SEQ ID NO: 22)
NNYGYGYDYYDYSYQQ,              (SEQ ID NO: 23)
NKYGYGYNYYDYSYSD,              (SEQ ID NO: 24)
AGYGYGYGYNYAYAYKA,             (SEQ ID NO: 25)
NTYRYGYGS,                     (SEQ ID NO: 26)
SRYGRYRYVQYGYTS,               (SEQ ID NO: 27)
SAYQDYGYYEYEYKS,               (SEQ ID NO: 28)
TGYQDYGYYEYEYQS,               (SEQ ID NO: 29)
and
SRYSGYYHYQAYYGE.               (SEQ ID NO: 30)
```

15. The compound of claim 12, comprising a peptide moiety having a sequence selected from the group consisting of:

```
KYGVYGFYGN,                    (SEQ ID NO: 32)
SYYHY,                         (SEQ ID NO: 32)
HYGYSY,                        (SEQ ID NO: 33)
AYSYGYNYYGYS,                  (SEQ ID NO: 34)
NYGYGYDYYDYS,                  (SEQ ID NO: 35)
KYGYGYNYYDYS,                  (SEQ ID NO: 36)
GYGYGYGYNYAY,                  (SEQ ID NO: 37)
and
DYGYYEYE.                      (SEQ ID NO: 38)
```

16. A compound having formula:

```
KYGVYGFYGNK(PNA(A))            (SEQ ID NO: 46)
SYYHYK(PNA(A))                 (SEQ ID NO: 47)
HYGYSYK(PNA(A))                (SEQ ID NO: 48)
AYSYGYNYYGYSK(PNA(A))          (SEQ ID NO: 49)
NYGYGYDYYDYSK(PNA(A))          (SEQ ID NO: 50)
KYGYGYNYYDYSK(PNA(A))          (SEQ ID NO: 51)
GYGYGYGYNYAYK(PNA(A))          (SEQ ID NO: 52)
DYGYYEYEK(PNA(A))              (SEQ ID NO: 53)
SASYYAY K(PNA(A))GTD           (SEQ ID NO: 62)
ESSYGAY K(PNA(A))GTD           (SEQ ID NO: 63)
KHSEYGY K(PNA(A))GTK           (SEQ ID NO: 64)
YNYYGYS K(PNA(A))SEK           (SEQ ID NO: 65)
KHSEGEY K(PNA(A))ETK           (SEQ ID NO: 66)
SSSYYHY K(PNA(A))GDE           (SEQ ID NO: 67)
VYGFYGN K(PNA(A))GKK           (SEQ ID NO: 68)
KYGVYGFYGNG(PNA(A))            (SEQ ID NO: 54)
SYYHYG(PNA(A))                 (SEQ ID NO: 55)
HYGYSYG(PNA(A))                (SEQ ID NO: 56)
AYSYGYNYYGYSG(PNA(A))          (SEQ ID NO: 57)
NYGYGYDYYDYSG(PNA(A))          (SEQ ID NO: 58)
KYGYGYNYYDYSG(PNA(A))          (SEQ ID NO: 59)
GYGYGYGYNYAYG(PNA(A))          (SEQ ID NO: 60)
or
DYGYYEYEG(PNA(A))              (SEQ ID NO: 61)
``` wherein PNA(A) is an adenine peptide analogue of general formula (XLI):

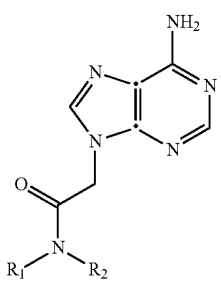

(XLI)

wherein:
- $R_1$ and $R_2$ are independently an alkyl substituted with a carboxyl, carbonyl, alcohol or primary amino;
- Wherein PNA(A) is linked to the peptide moiety by formation of a peptide bond with a N-terminal $NH_2$ group or a C-terminal COOH group of Lys or with an amino group in the side chain of Gly.

17. The compound of claim 12, wherein in $R_1$ and $R_2$ the alkyl is a straight chain hydrocarbon of 1 to 5 carbon atoms.

18. The compound of claim 17, wherein in Formula (XLI), $R_1$ is —$CH_2CH_2NH_2$.

19. The compound of claim 17, wherein in Formula (XLI), $R_2$ is —$CH_2C(O)OH$.

20. The compound of claim 17, wherein in Formula (XLI), $R_1$ is —$CH_2CH_2NH_2$ and $R_2$ is —$CH_2C(O)OH$.

21. The compound of claim 12, which comprises a peptide moiety and wherein $R_2$ is an alkyl substituted with —C(O)O~, —C(O)~, or —C(O)R'~, where R' is alkyl or H, —O~ and —NH~; wherein ~ represents the bond attaching PNA(A) to the peptide moiety.

22. The compound of claim 1, wherein the peptide moiety comprises a fragment of at least 4 amino acid residues of a sequence as depicted on SEQ ID NO: 1, 2, 3, 4, 5, 6, 7, 8, 9, 10, 11, 12, 13 or 14.

23. The compound of claim 1, wherein the compound has a number of amino acid residues between 5 and 15.

24. The compound of claim 14, wherein the peptide moiety comprises a fragment of at least 4 amino acid residues selected from the group consisting of sequence SEQ ID NO: 15, 16, 17, 18, 19, 20, 21, 22, 23, 24, 25, 26, 27, 28, 29 and 30.

25. The compound of claim 15, wherein the peptide moiety comprises a fragment of at least 4 amino acid residues selected from the group consisting of SEQ ID NO: 31, 32, 33, 34, 35, 36, 37 and 38.

26. The compound of claim 16, wherein in $R_1$ and $R_2$ the alkyl is a straight chain hydrocarbon of 1 to 5 carbon atoms.

27. The compound of claim 16, wherein $R_2$ is an alkyl substituted with —C(O)O~, —C(O)~, or —C(O)R'~, where R' is alkyl or H, —O~ and —NH~; wherein ~ represents the bond attaching PNA(A) to the peptide moiety.

28. A compound comprising a peptide moiety comprising the peptide sequence of a tyrosine cluster YC of the BY-kinase of a bacteria, and an adenine peptide analogue PNA (A), whereas the peptide moiety and the PNA are linked together.

29. A compound comprising a peptide moiety comprising the peptide sequence of a tyrosine cluster YC of the BY-kinase of a bacteria, and an adenine peptide analogue PNA (A), whereas the peptide moiety and the PNA are linked together and the YC is as depicted on SEQ ID NO:15, 16, 17, 18, 19, 20, 21, 22, 23, 24, 25, 26, 27, 28, 29 or 30.

30. A compound comprising a peptide moiety comprising the peptide sequence of a tyrosine cluster YC of the BY-kinase of a bacteria, and an adenine peptide analogue PNA (A), whereas the peptide moiety and the PNA are linked together and the peptide moiety comprises a fragment of at least 4 amino acid residues of the YC as depicted on SEQ ID NO:15, 16, 17, 18, 19, 20, 21, 22, 23, 24, 25, 26, 27, 28, 29 or 30.

31. A compound comprising a peptide moiety consisting essentially of the peptide sequence of a tyrosine cluster YC of the BY-kinase of a bacteria, and an adenine peptide analogue PNA(A), whereas the peptide moiety and the PNA are linked together and the peptide moiety comprises a sequence as depicted on SEQ ID NO:15, 16, 17, 18, 19, 20, 21, 22, 23, 24, 25, 26, 27, 28, 29 or 30.

32. A compound comprising a peptide moiety comprising the peptide sequence of a tyrosine cluster YC of the BY-kinase of a bacteria, and an adenine peptide analogue PNA (A), whereas the peptide moiety and the PNA are linked together and the YC is as depicted on SEQ ID NO: 31, 32, 33, 34, 35, 36, 37, or 38.

33. A compound comprising a peptide moiety consisting essentially of the peptide sequence of a tyrosine cluster YC of the BY-kinase of a bacteria, and an adenine peptide analogue PNA(A), whereas the peptide moiety and the PNA are linked together and the peptide moiety comprises a sequence as depicted on SEQ ID NO: 31, 32, 33, 34, 35, 36, 37 or 38.

34. A compound comprising a peptide moiety comprising the peptide sequence of a tyrosine cluster YC of the BY-kinase of a bacteria, and an adenine peptide analogue PNA (A), whereas the peptide moiety and the PNA are linked together and the peptide moiety comprises moiety comprises a fragment of at least 4 amino acid residues of a sequence as depicted on SEQ ID NO: 31, 32, 33, 34, 35, 36, 37 or 38.

\* \* \* \* \*